(12) United States Patent
Urech et al.

(10) Patent No.: US 8,227,199 B2
(45) Date of Patent: Jul. 24, 2012

(54) METHODS FOR IDENTIFYING IMMUNOBINDERS OF CELL-SURFACE ANTIGENS

(75) Inventors: David Urech, Hombrechtikon (CH); Valerie Hulmann-Cottier, Zurich (CH)

(73) Assignee: ESBATech, an Alcon Biomedical Research Unit, LLC, Schlieren (CH)

( * ) Notice: Subject to any disclaimer, the term of this patent is extended or adjusted under 35 U.S.C. 154(b) by 107 days.

(21) Appl. No.: 12/710,579

(22) Filed: Feb. 23, 2010

(65) Prior Publication Data

US 2010/0216170 A1 Aug. 26, 2010

Related U.S. Application Data

(60) Provisional application No. 61/155,105, filed on Feb. 24, 2009, provisional application No. 61/155,041, filed on Feb. 24, 2009.

(51) Int. Cl.
- *G01N 33/53* (2006.01)
- *G01N 33/567* (2006.01)
- *G01N 1/30* (2006.01)
- *G01N 33/48* (2006.01)

(52) U.S. Cl. ..................... 435/7.2; 435/40.51

(58) Field of Classification Search .................. None
See application file for complete search history.

(56) References Cited

U.S. PATENT DOCUMENTS

| | | | |
|---|---|---|---|
| 5,225,539 | A | 7/1993 | Winter |
| 6,300,064 | B1 | 10/2001 | Knappick et al. |
| 6,815,540 | B1 | 11/2004 | Pluckthun et al. |
| 2004/0132028 | A1 | 7/2004 | Stumpp et al. |
| 2005/0033031 | A1 | 2/2005 | Couto |
| 2007/0134249 | A1 | 6/2007 | Denney et al. |

FOREIGN PATENT DOCUMENTS

| | | |
|---|---|---|
| CA | 2350078 | 5/2000 |
| DE | 10314412 A1 | 10/2004 |
| EP | 1230932 A2 | 8/2002 |
| EP | 1918302 A | 5/2008 |
| FR | 2777007 A1 | 10/1999 |
| WO | WO0029442 A1 | 5/2000 |
| WO | WO2008006235 A | 1/2008 |
| WO | WO2008076487 A2 | 6/2008 |
| WO | 2009155726 A2 | 12/2009 |

OTHER PUBLICATIONS

Feldhaus MJ, et al. J. Immunological Methods 290:69-80, 2004.*
Zhou C, et al. mAbs 2(5):508-518, 2010.*
Beerli RR, et al. PNAS 105(38):14336-14341, Sep. 23, 2008.*
Corisdeo S, et al. Protein Expression and Purification 34:270-279, 2004.*
Kaija Alfthan, et al., "Properties of a Single-Chain Antibody Containing Different Linker Peptides," Protein Engineering, 1995, pp. 725-731, vol. 8, No. 7.
Leandros Arvanitakis, et al., "Human Herpesvirus KSHV Encodes a Constitutively Active G-Protein-Coupled Receptor Linked to Cell Proliferation," Nature, 1997. pp. 347-350, vol. 385, No. 23.
Robert E. Bird, et al., "Single-Chain Antigen-Binding Proteins," Science, 1988, pp. 423-426, vol. 242.
David C. Brummell, et al., "Probing the Combining Site of an Anti-Carbohydrate Antibody by Saturation-Mutagensis: Role of the Heavy-Chain CDR3 Residues," Biochemistry, 1993, pp. 1180-1187, vol. 32.
Elizabeth A. Burks, et al., "In Vitro Scanning Saturation Mutagensis of an Antibody Binding Pocket," Proc. Natl. Acad. Sci. USA, 1997, pp. 412-417, vol. 94.
James L. Cornette, et al., "Hydrophobicity Scales and Computational Techniques for Detecting Amphipathic Structures in Proteins," J. Mel. Biol., 1987, pp. 659-685, vol. 195.
Susanna Cotecchia, et al., "Discrete Amino Add Sequences of the α1-Adrenergic Receptor Determine the Selectivity of Coupling to Phosphatidylinositol," J. Biol. Chem., 1992, pp. 1633-1639, vol. 267, No. 3.
Meinrad P. Gawaz, et al., "Ligand Bridging Mediates Integrin αIIbβ3 (Platelet GPIIB-IIIA) Dependent Homotypic and Heterotypic Cell-Cell Interactions," J. Clin. Invest., 1991, pp. 1128-1134, vol. 88.
Ulrik Gether, et al., "G Protein-Coupled Receptors," J. Biol. Chem., 1998, pp. 17979-17982, vol. 273.
C. Hamers-Casterman, et al., "Naturally Occurring Antibodies Devoid of Light Chambers," Nature, 1993, pp. 446-448, vol. 363.
Michael A. Kjelsberg, et al., "Constitutive Activation of the α1B-Adrenergic Receptor by All Amino Acid Substitutions at a Single Site," J. Biol. Chem., 1992, pp. 1430-1433, vol. 267.
Hiroyuki Kobayashi, et al., "Tryptophari H33 Plays an Important Role in Pyrimidine (6-4) Pyrimidone Photoproduct Binding by a High-Affinity Antibody." Protein Engineering, 1999, pp. 879-884, vol. 12, No. 10.
Evi Kostenis, et al., "Molecular Basis of Receptor/G Protein Coupling Selectivity Studied by Coexpression of Wild Type and Mutant m2 Muscarinic Receptors with Mutant Gaq Subunits," Biochemistry, 1997, pp. 1487-1495, vol. 36.
Cheng-Mee Leong, et al., "A Flow Cytometry-Based Assay for the Measurement of Protein Regulation of E-Cadherin-Mediated Adhesion," Journal of Immunological Methods, 2005,pp. 116-124, vol. 302.
Louis M. Luttrell, et al., "Antagonism of Catecholamine Receptor Signaling by Expression of Cytoplasmic Domains of the Receptors," Science, 1993, pp. 1453-1457, vol. 259.
Philip M. Murphy, "The Molecular Biology of Leukocyte Chemoattractant Receptors," Annu. Rev. Immunol., 1994, pp. 593-633, vol. 12.
Eugene W. Myers, et al., "Optimal Alignments in Linear Space," Comput. Appl. Biosci., 1988, pp. 11-17, vol. 4.
Takashi Okamoto, et al., "Identification of a Gs Activator Region of the B2-Adrenergic Receptor That is Autoregulated Via Protein Kinase A-Dependent Phosphorylation," Cell, 1991, pp. 723-730, vol. 67.

(Continued)

*Primary Examiner* — Robert Landsman
(74) *Attorney, Agent, or Firm* — Jason J. Derry

(57) ABSTRACT

The invention provides methods for identifying immunobinders, such as scFv antibodies, capable of specifically binding to cell surface antigens, and compositions identified according to said methods.

22 Claims, 8 Drawing Sheets

OTHER PUBLICATIONS

Krzysztof Palczewski, et al., "Crystal Structure of Rhodopsin: A G Protein-Coupled Receptor," Science, 2000, pp. 739-745, vol. 289.

Porntula Panorchan, et al., "Single-Molecule Analysis of Cadherin-Mediated Cell-Cell Adhesion," J. Cell Science, 2006, pp. 66-74, vol. 119.

George D. Rose, et al., "Hydrophobicity of Amino Acid Residues in Globular Proteins," Science, 1985, pp. 834-838, vol. 229.

Bernie Scallon, et al., "Binding and Functional Comparisons of Two Types of Tumor Necrosis Factor Antagonists," The Journal of Pharmacology and Experimental Therapeutics, 2002, pp. 418-426, vol. 301, No. 2.

Catherine D. Strader, et al., "Structure and Function of G Protein-Coupled Receptors," Annu. Rev. Biochem., 1994, pp. 101-132, vol. 63.

Catherine D. Strader, et al., "The Family of G-Protein-Coupled Receptors," FASEB J., 1995, pp. 745-754, vol. 9.

Rudolf H. Zubler, et al., "Mutant EL-4 Thymoma Cells Polyclonally Activate Murine and Human B Cells Via Direct Cell Interaction," The Journal of Immunology, 1985, vol. 134, No. 6.

L. F. Erdile, et al., "Whole cell ELISA for Detection of Tumor Antigen Expression in Tumor Samples," Journal of Immunological Methods, Dec. 1, 2001, pp. 47-53, vol. 258(1-2).

D. D. Smith, et al., "Optimization of Cellular ELISA for Assay of Surface Antigens on Human Synoviocytes," Biotechniques, May 1997, pp. 952-957, vol. 22(5).

M. R. Bono, et al., "A Flow Cytometric Procedure for Quantification of Cell Adhesion in Complex Mixtures of Cells," Journal of Immunological Methods, Feb. 1, 1999, pp. 27-36, vol. 223(1).

Michael Ottiger, et al., "Efficient Intraocular Penetration of Topical Anti-TNF-Alpha Single Chain Antibody (ESBA105) to Anterior and Posterior Segment Without Penetration Enhancer," Investigative Ophthalmology & Visual Science, Feb. 1, 2009, pp. 779-786, vol. 50(2).

Esther Furrer, et al., "Pharmacokinetics and Posterior Segment Biodistribution of ESBA105, an Anti-TNF-Alpha Single-Chain Antibody, Upon Topical Administration to the Rabbit," Investigative Ophthalmology & Visual Science, Feb. 1, 2009, pp, 771-778.

K. L. Wark, et al., "Latest Technologies for the Enhancement of Antibody Affinity," Advanced Drug Delivery Reviews, 2006, pp. 657-670, vol. 58(5-6).

International Search Report corresponding to PCT Application Serial No. PCT/CH2010/000044 dated Jun. 6, 2010.

Callewaert et al.; "Characterization of effector-target conjugates for cloned human natural killer and human lymphokine activated killer cells by flow cytometry"; Cytometry; vol. 12; pp. 666-676 (1991).

Radcliff et al.; "Quantificatin of effector/target conjugation involving natural killer (NK) or lymphokine activated killer (LAK) cells by two-color flow cytometry"; Journal of Immunological Methods; vol. 139; pp. 281-292 (1991).

Berke: "Enumeration of lymphocyte-target cell conjugates by cytofluorometry"; Eur. J. Immunology; vol. 15; pp. 337-349 (1985).

Denizot et al.: "Clonal expansion of LT cells: A cytotoxic T-cell response in vivo that involves precursor cell proliferation"; Proc. Natl. Acad. Sci.; vol. 83; pp. 6089-6092 (Aug. 1986).

Lebow et al.: "Analysis of lymphocyte-target conjugates by flow cytometry"; Nat. Immun. Cell Growth Regul.; vol. 5; pp. 221-237 (1986).

Muehlinghaus et al.; "Regulation of CXCR3 and CXCR4 expression during terminal differentiation of memory B cells into plasma cells"; Blood; vol. 105; pp. 3965-3971 (2005).

Segal and Stephany; "The measurement of specific cell:cell interactions by dual-parameter flow cytometry"; Cytometry; vol. 5; pp. 169-181 (1984).

Nimmerjahn and Ravetch; "Analyzing Antibody-Fc-Receptor Interactions"; Methods in Molecular Biology; vol. 415; pp. 151-162 (2008).

Segal and Stephany; " The Mechanism of Intercellular Aggregation: I: The Kinetics of the FCγ Receptor-Mediated Aggregation of P388D, Cells With Antibody-Coated Lymphocytes at 4C"; The Journal of Immunology; vol. 132; No. 4; pp. 1924-1930 (Apr. 1984).

\* cited by examiner

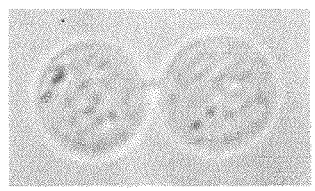
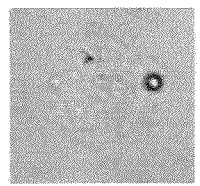
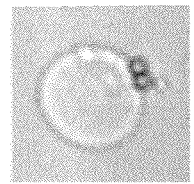
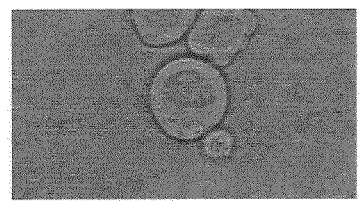
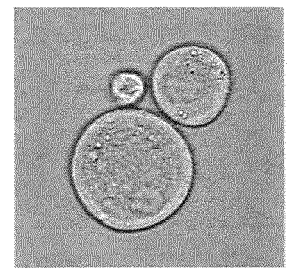
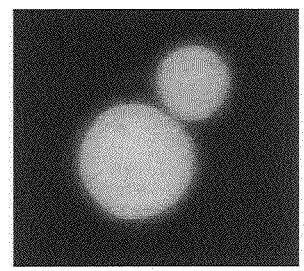
FIG. 7  FIG. 8a  FIG. 8b

SEQUENCE LISTING

```
<160> NUMBER OF SEQ ID NOS: 10

<210> SEQ ID NO 1
<211> LENGTH: 232
<212> TYPE: PRT
<213> ORGANISM: Artificial Sequence
<220> FEATURE:
<223> OTHER INFORMATION: variable heavy chain framework of FW1.4 (a43)
<220> FEATURE:
<221> NAME/KEY: CDR
<222> LOCATION: (26)..(75)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (90)..(139)
<223> OTHER INFORMATION: CDR; at least 1 and up to 50 amino acids can be
      present or absent. Xaa can be any naturally occurring amino acid.
<220> FEATURE:
<221> NAME/KEY: CDR
```

```
<222> LOCATION: (172)..(221)
<223> OTHER INFORMATION: CDR; at least 1 and up to 50 amino acids can be
      present or absent. Xaa can be any naturally occurring amino acid.

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Ser Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Arg Phe Thr Ile Ser
    130                 135                 140

Arg Asp Asn Ser Lys Asn Thr Leu Tyr Leu Gln Met Asn Ser Leu Arg
145                 150                 155                 160

Ala Glu Asp Thr Ala Val Tyr Tyr Cys Ala Lys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 2
<211> LENGTH: 231
<212> TYPE: PRT
<213> ORGANISM: Artificial Sequence
<220> FEATURE:
<223> OTHER INFORMATION: variable light chain framework of FW1.4 (KI27)
<220> FEATURE:
<221> NAME/KEY: CDR
<222> LOCATION: (24)..(73)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (89)..(138)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (171)..(220)
<223> OTHER INFORMATION: CDR; at least 1 and up to 50 amino acids can be
      present or absent. Xaa can be any naturally occurring amino acid.

<400> SEQUENCE: 2

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
```

-continued

```
                    20                  25                  30
Xaa Xaa Xaa Xaa Xaa Xaa Xaa Xaa Xaa Xaa Xaa Xaa Xaa Xaa Xaa
        35                  40                  45
Xaa Xaa Xaa Xaa Xaa Xaa Xaa Xaa Xaa Xaa Xaa Xaa Xaa Xaa Xaa
    50                  55                  60
Xaa Xaa Xaa Xaa Xaa Xaa Xaa Xaa Trp Tyr Gln Gln Lys Pro Gly
65                  70                  75                  80
Lys Ala Pro Lys Leu Leu Ile Tyr Xaa Xaa Xaa Xaa Xaa Xaa Xaa
                85                  90                  95
Xaa Xaa Xaa Xaa Xaa Xaa Xaa Xaa Xaa Xaa Xaa Xaa Xaa Xaa Xaa
            100                 105                 110
Xaa Xaa Xaa Xaa Xaa Xaa Xaa Xaa Xaa Xaa Xaa Xaa Xaa Xaa Xaa
        115                 120                 125
Xaa Xaa Xaa Xaa Xaa Xaa Xaa Xaa Xaa Gly Val Pro Ser Arg Phe
    130                 135                 140
Ser Gly Ser Gly Ser Gly Ala Glu Phe Thr Leu Thr Ile Ser Ser Leu
145                 150                 155                 160
Gln Pro Asp Asp Phe Ala Thr Tyr Tyr Cys Xaa Xaa Xaa Xaa Xaa Xaa
                165                 170                 175
Xaa Xaa Xaa Xaa Xaa Xaa Xaa Xaa Xaa Xaa Xaa Xaa Xaa Xaa Xaa
            180                 185                 190
Xaa Xaa Xaa Xaa Xaa Xaa Xaa Xaa Xaa Xaa Xaa Xaa Xaa Xaa Xaa
        195                 200                 205
Xaa Xaa Xaa Xaa Xaa Xaa Xaa Xaa Xaa Xaa Xaa Phe Gly Gln Gly
    210                 215                 220
Thr Lys Leu Thr Val Leu Gly
225                 230

<210> SEQ ID NO 3
<211> LENGTH: 483
<212> TYPE: PRT
<213> ORGANISM: Artificial Sequence
<220> FEATURE:
<223> OTHER INFORMATION: framework of FW1.4
<220> FEATURE:
<221> NAME/KEY: CDR
<222> LOCATION: (24)..(73)
<223> OTHER INFORMATION: CDR; at least one and up to 50 amino acids can
      be present of absent. Xaa can be any naturally occurring amino
      acid.
<220> FEATURE:
<221> NAME/KEY: CDR
<222> LOCATION: (89)..(138)
<223> OTHER INFORMATION: CDR; at least one and up to 50 amino acids can
      be present of absent. Xaa can be any naturally occurring amino
      acid.
<220> FEATURE:
<221> NAME/KEY: CDR
<222> LOCATION: (171)..(220)
<223> OTHER INFORMATION: CDR; at least one and up to 50 amino acids can
      be present of absent. Xaa can be any naturally occurring amino
      acid.
<220> FEATURE:
<221> NAME/KEY: CDR
<222> LOCATION: (277)..(326)
<223> OTHER INFORMATION: CDR; at least one and up to 50 amino acids can
      be present of absent. Xaa can be any naturally occurring amino
      acid.
<220> FEATURE:
<221> NAME/KEY: CDR
<222> LOCATION: (341)..(390)
<223> OTHER INFORMATION: CDR; at least one and up to 50 amino acids can
      be present of absent. Xaa can be any naturally occurring amino
      acid.
<220> FEATURE:
<221> NAME/KEY: CDR
```

<222> LOCATION: (423)..(472)
<223> OTHER INFORMATION: CDR; at least one and up to 50 amino acids can be present of absent. Xaa can be any naturally occurring amino acid.

<400> SEQUENCE: 3

```
Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly Gly
225                 230                 235                 240

Ser Gly Gly Gly Gly Ser Gly Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Xaa Xaa Xaa Xaa Xaa Xaa Xaa Xaa Xaa Xaa Xaa
275                 280                 285

Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Trp Val Arg Gln Ala Pro Gly Lys Gly Leu
            325                 330                 335

Glu Trp Val Ser Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa
        370                 375                 380

Xaa Xaa Xaa Xaa Xaa Xaa Arg Phe Thr Ile Ser Arg Asp Asn Ser Lys
```

```
                385                 390                 395                 400
Asn Thr Leu Tyr Leu Gln Met Asn Ser Leu Arg Ala Glu Asp Thr Ala
                405                 410                 415

Val Tyr Tyr Cys Ala Lys Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 4
<211> LENGTH: 232
<212> TYPE: PRT
<213> ORGANISM: Artificial Sequence
<220> FEATURE:
<223> OTHER INFORMATION: variable heavy chain framework of rFW1.4
<220> FEATURE:
<221> NAME/KEY: CDR
<222> LOCATION: (26)..(75)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (90)..(139)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (172)..(221)
<223> OTHER INFORMATION: CDR; at least 1 and up to 50 amino acids can be
      present or absent. Xaa can be any naturally occurring amino acid.

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Thr Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Arg Phe Thr Ile Ser
    130                 135                 140

Arg Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190
```

```
Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
        210                 215                 220

Gly Thr Leu Val Thr Val Ser Ser
225                 230

<210> SEQ ID NO 5
<211> LENGTH: 483
<212> TYPE: PRT
<213> ORGANISM: Artificial Sequence
<220> FEATURE:
<223> OTHER INFORMATION: framework of rFW1.4
<220> FEATURE:
<221> NAME/KEY: CDR
<222> LOCATION: (24)..(73)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (89)..(138)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (171)..(220)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (277)..(326)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (341)..(390)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (423)..(472)
<223> OTHER INFORMATION: CDR; at least 1 and up to 50 amino acids can be
      present or absent. Xaa can be any naturally occurring amino acid.

<400> SEQUENCE: 5

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
```

```
                    165                 170                 175
Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
                195                 200                 205

Xaa Xaa Xaa Xaa Xaa Xaa Xaa Xaa Xaa Xaa Xaa Phe Gly Gln Gly
                210                 215                 220

Thr Lys Leu Thr Val Leu Gly Gly Gly Gly Ser Gly Gly Gly Gly
225                 230                 235                 240

Ser Gly Gly Gly Ser Gly Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Thr Ala Ser Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa Xaa Xaa Xaa Xaa Xaa Xaa
                370                 375                 380

Xaa Xaa Xaa Xaa Xaa Xaa Arg Phe Thr Ile Ser Arg Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa
                435                 440                 445

Xaa Xaa Xaa Xaa Xaa Xaa Xaa Xaa Xaa Xaa Xaa Xaa Xaa Xaa Xaa
                450                 455                 460

Xaa Xaa Xaa Xaa Xaa Xaa Xaa Trp Gly Gln Gly Thr Leu Val Thr
465                 470                 475                 480

Val Ser Ser

<210> SEQ ID NO 6
<211> LENGTH: 231
<212> TYPE: PRT
<213> ORGANISM: Artificial Sequence
<220> FEATURE:
<223> OTHER INFORMATION: variable heavy chain framework of rFW1.4(V2)
<220> FEATURE:
<221> NAME/KEY: CDR
<222> LOCATION: (26)..(75)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (90)..(138)
<223> OTHER INFORMATION: CDR; at least 1 and up to 50 amino acids can be
      present or absent. Xaa can be any naturally occurring amino acid.
<220> FEATURE:
<221> NAME/KEY: CDR
```

```
<222> LOCATION: (171)..(220)
<223> OTHER INFORMATION: CDR; at least 1 and up to 50 amino acids can be
      present or absent. Xaa can be any naturally occurring amino acid.

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Thr Val Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Arg Phe Thr Ile Ser Lys
    130                 135                 140

Asp Thr Ser Lys Asn Thr Val Tyr Leu Gln Met Asn Ser Leu Arg Ala
145                 150                 155                 160

Glu Asp Thr Ala Val Tyr Tyr Cys Ala Arg Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln Gly
    210                 215                 220

Thr Leu Val Thr Val Ser Ser
225                 230

<210> SEQ ID NO 7
<211> LENGTH: 483
<212> TYPE: PRT
<213> ORGANISM: Artificial Sequence
<220> FEATURE:
<223> OTHER INFORMATION: framework of rFW1.4(V2)
<220> FEATURE:
<221> NAME/KEY: CDR
<222> LOCATION: (24)..(73)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (89)..(138)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (171)..(220)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (277)..(326)
<223> OTHER INFORMATION: CDR; at least 1 and up to 50 amino acids can be
      present or absent. Xaa can be any naturally occurring amino acid.
<220> FEATURE:
<221> NAME/KEY: CDR
```

-continued

```
<222> LOCATION: (341)..(390)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (423)..(472)
<223> OTHER INFORMATION: CDR; at least 1 and up to 50 amino acids can be
      present or absent. Xaa can be any naturally occurring amino acid.

<400> SEQUENCE: 7

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly Gly
225                 230                 235                 240

Ser Gly Gly Gly Gly Ser Gly Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Thr Val Ser Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
        355                 360                 365
```

-continued

```
Xaa Xaa Xaa Xaa Xaa Xaa Xaa Xaa Xaa Xaa Xaa Xaa Xaa
    370                 375                 380

Xaa Xaa Xaa Xaa Xaa Xaa Arg Phe Thr Ile Ser Lys Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 8
<211> LENGTH: 20
<212> TYPE: PRT
<213> ORGANISM: Artificial Sequence
<220> FEATURE:
<223> OTHER INFORMATION: linker

<400> SEQUENCE: 8

Gly Gly Gly Gly Ser Gly Gly Gly Gly Ser Gly Gly Gly Gly Ser Gly
1               5                   10                  15

Gly Gly Gly Ser
            20

<210> SEQ ID NO 9
<211> LENGTH: 231
<212> TYPE: PRT
<213> ORGANISM: Artificial Sequence
<220> FEATURE:
<223> OTHER INFORMATION: substituted variable light chain framework of
      FW1.4
<220> FEATURE:
<221> NAME/KEY: CDR
<222> LOCATION: (24)..(73)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (89)..(138)
<223> OTHER INFORMATION: CDR; at least 1 and up to 50 amino acids can be
      present or absent. Xaa can be any naturally occurring amino acid.
<220> FEATURE:
<221> NAME/KEY: CDR
<222> LOCATION: (171)..(220)
<223> OTHER INFORMATION: CDR; at least 1 and up to 50 amino acids can be
      present or absent. Xaa can be any naturally occurring amino acid.

<400> SEQUENCE: 9

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80
```

```
-continued

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 10
<211> LENGTH: 5
<212> TYPE: PRT
<213> ORGANISM: Artificial Sequence
<220> FEATURE:
<223> OTHER INFORMATION: linker

<400> SEQUENCE: 10

Gly Gly Gly Gly Ser
1               5
```

METHODS FOR IDENTIFYING IMMUNOBINDERS OF CELL-SURFACE ANTIGENS

CROSS-REFERENCE TO RELATED APPLICATIONS

The present application claims priority from U.S. Provisional Application Ser. No. 61/155,041 filed Feb. 24, 2009; U.S. Provisional Application Ser. No. 61/155,105 filed Feb. 24, 2009; Swiss Patent Application Serial No.: CH/00832/09 filed Jun. 2, 2009; and PCT Application Serial No.: PCT/CH2009/000222 filed Jun. 25, 20009, the entire contents of which are incorporated herein by reference.

BACKGROUND INFORMATION

Immunobinders, including antibodies, their conjugates and derivatives are hugely commercially important as therapeutic and diagnostic agents. Traditional methods for antibody preparation or screening usually utilize soluble antigens. However, for certain membrane-bound protein antigens, the conformational epitopes on the antigens are altered if the antigens are solubilized from the membrane, resulting in the failure of antibody preparation or screening. In addition, one major problem in immunoblotting and affinity chromatography methods is that antibodies with a moderate affinity for the antigen will be selected. This allows the inclusion of many cross-reactive or sticky antibodies, causing burdens in the sequential screening procedures. Although cells expressing membrane-bound antigens have been used directly for antibody preparation, an efficient screening method capable of detecting and enriching high affinity antibodies against cell-surface antigens is still lacking.

SUMMARY OF THE INVENTION

The invention provides methods for identifying immunobinders, such as scFv antibodies, capable of specifically binding to cell surface antigens. The methods of the invention generally comprise contacting labeled antigen-expressing cells with labeled immunobinder-expressing cells and isolating immunobinder-expressing cells that bind to the antigen-expressing cells using a cell sorter. These methods are particularly useful for the rapid and efficient identification of immunobinders against conformational epitopes present in integral membrane proteins, such as GPCRs. The invention also provides isolated immunobinders and immunobinder-encoding nucleic acids identified using the methods of the invention.

In one aspect the invention provides a method for identifying an immunobinder that specifically binds to a cell surface antigen of interest. The method comprises: providing a plurality of immunobinder-expressing cells operably linked a first sortable label; providing a plurality of antigen-expressing cells operably linked to a second sortable label, wherein the antigen of interest is displayed at the surface of the antigen expressing cell; contacting the antigen-expressing cells with the immunobinder-expressing cells; and separating from the plurality of immunobinder-expressing cells, one or more immunobinder-expressing cells that can specifically bind to the antigen-expressing cells using a cell sorter (e.g., a fluorescence activated cell sorter), wherein the presence of the first and second sortable label in a single cellular complex (e.g., a complex formed between an antigen and a B-cell receptor) is indicative of the binding of an immunobinder-expressing cell to an antigen-expressing cell, thereby identifying an immunobinder that binds to a antigen of interest.

In some embodiments, the separated immunobinder-expressing cells are clonally isolated. In some embodiments, the immunobinder-expressing cells are subjected to clonal expansion. In other embodiments, the immunobinder-encoding nucleic acid sequence is isolated from immunobinder-expressing cells. Suitable methods for isolation of the immunobinder-encoding nucleic acid sequence include PCR, e.g., single-cell PCR. The immunobinder-encoding nucleic acid sequence can be isolated after the cells are clonally isolated and/or after clonal expansion.

In some embodiments, immunobinder-expressing cells isolated using the methods of the invention are subjected to a cell-based assays in order to functionally characterize the immunobinder. Suitable cell-based assays include CELISA.

In some embodiments, the immunobinder is an antibody. Such antibodies include, mouse, rabbit, rabbitized, chicken, camel, camelized, human, humanized and chimeric antibodies. Suitable antibody formats include, without limitation, Fab, Dab, Nanobody and scFv.

In some embodiments, the antigen of interest is expressed from an exogenous gene. In other embodiments, the antigen of interest is a genetically engineered antigen. In other embodiments, the antigen of interest is an integral membrane protein. Suitable integral membrane proteins include, without limitation, GPCRs (e.g., CXCR2) or ion channels.

In some embodiments, the first or second sortable label is a fluorescent label. Suitable fluorescent labels include, without limitation, fluorescent proteins, antibody/fluor conjugates and fluorescent cellular labels.

In some embodiments, the antigen-expressing cells are yeast or mammalian cells (e.g., human cells). In some embodiments, the antigen-expressing cells express an exogenous antigen. In some embodiments the antigen-expressing cells are transfected with an expression vector.

In some embodiments, the immunobinder-expressing cells are yeast or mammalian cells. Suitable mammalian cells include, without limitation, B-cells, e.g., rabbit B-cells. In some embodiments the B-cells are isolated from an immunized animal, e.g., an animal immunized by DNA vaccination. In some embodiments, the immunobinder-expressing cells comprise an immunobinder expressed from an expression vector.

In another aspect, the invention provides an isolated nucleic acid molecule encoding an immunobinder identified by the methods of the invention.

In another aspect, the invention provides a method of producing an immunobinder capable of binding to an antigen of interest, comprising introducing an immunobinder-encoding nucleic acid sequence identified by the methods of the invention into an expression environment such that the encoded immunobinder is produced.

In another aspect, the invention provides an immunobinder produced by the methods of the invention.

In another aspect, the invention also provides a method for identifying a B-cell clone that specifically binds to a cell surface antigen of interest comprising: immunizing an animal with DNA encoding a cell surface antigen; isolating B-cells from the immunized animal; labeling the B-cells with a first sortable label; providing a plurality of antigen-expressing cells operably linked to a second sortable label, wherein the antigen of interest is displayed at the surface of the antigen expressing cell; contacting the antigen-expressing cells with the B-cells; and separating from the plurality of B-cells, one or more B-cells that can specifically bind to the antigen-expressing cells using a cell sorter, wherein the presence of the first and second sortable label in a single cellular complex is indicative of the binding of an B-cell to an antigen-expressing cell, thereby identifying a B-cell clone that binds to a antigen of interest.

BRIEF DESCRIPTION OF THE FIGURES

FIG. 2A: Lymphocytes were gated according to forward and side scatter. FIG. 2B: Among them, IgG+ IgM− cells (probably memory B cells) were selected (shown circled). FIG. 2C: Cells double-stained with ESBA903-PE and ESBA903-PerCP (shown circled) were expected to encode high affinity IgGs against ESBA903. Cells showing the brightest fluorescence (uncircled) were sorted in 96-well plates.

FIG. 5a: FACS analysis of the 3 different CIO-TNFα—memory B cells suspensions. Top left: dot plot showing cell suspension forward and side scatter. The living cells, comprising a large population of transgenic CHO cells and a small population of memory B cells, were gated. Down left: dot plot showing APC and FITC fluorescence. Here, the memory B cells (IgG+/IgM−) were gated. These two dot plots were identical for all three samples; therefore, they are shown only once.

FIG. 5 b: histograms and population hierarchy of the 3 samples: top: CHO-TNFα cells+ESBA105+memory B cells of ESBA105 immunized rabbit; middle: CHO-TNFα cells+ESBA105+memory B cells of non-immunized rabbit; down: CHO-TNFα cells+memory B cells of ESBA105 immunized rabbit. On the histograms, memory B cells binding to CHO cells were gated.

FIG. 6a: dot plot showing cell suspension forward and side scatter. The living cells, comprising a large population of transgenic CHO cells and a small population of lymphocytes, were gated. FIG. 6b: dot plot showing APC and FITC fluorescence. Here, the memory B cells (IgG+/IgM−) were gated. FIG. 6c: histogram showing calcein fluorescence of gated memory B cells. Gated population was sorted (memory B cells binding to CHO-TNFα-ESBA105 complex).

FIG. 7: Bright field microscopy pictures of beads coated with anti-TNFα IgG which interact with CHO-TNFα (B220) transgenic cells.

FIGS. 8A-8B: Bright Field microscopy pictures (left column: FIG. 8a) and fluorescence microscopy pictures (right column: FIG. 8b) of CHO-TNFalpha/ESBA105 cells (big cells) bound to B cells, which have anti-ESBA105 antibodies on the surface (smaller cells).

DETAILED DESCRIPTION

Figure 1:
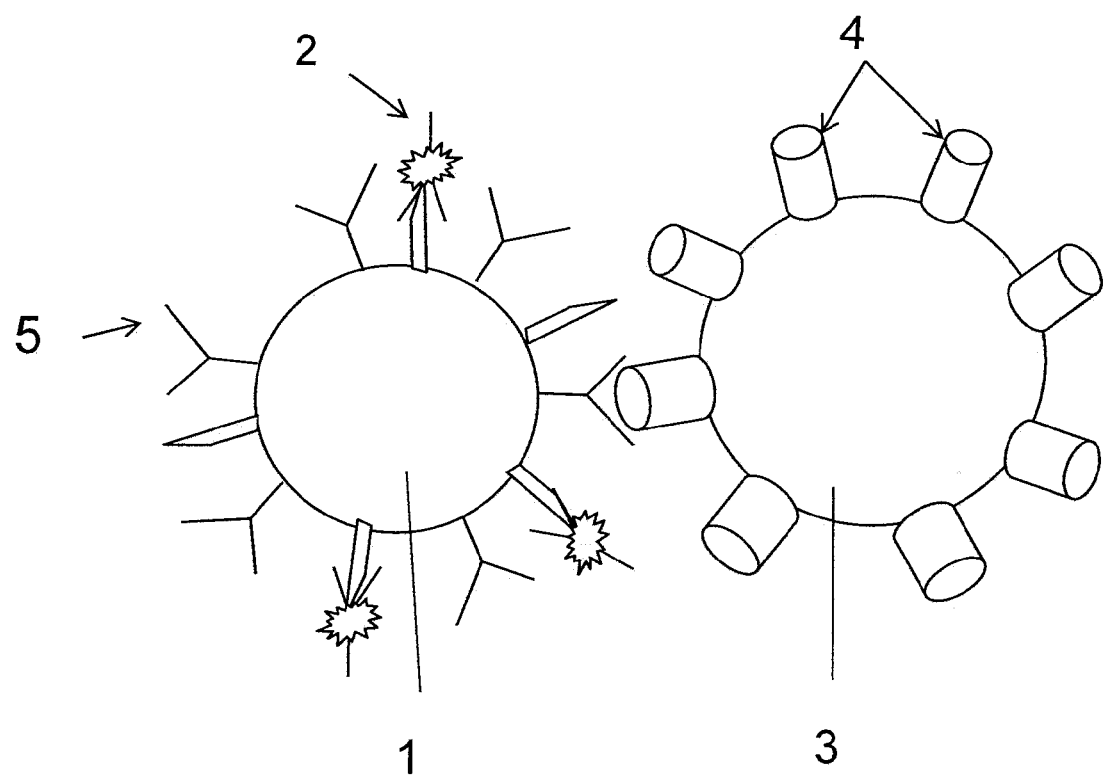
FIG. 1 schematically shows a B-cell 1 labeled with a fluorescent antibody 2 interacting with a target-expressing cell stained with an intracellular dye 3. (4: target of choice/antigen; 5: B cell receptor (BCR)).

The invention provides methods for identifying immunobinders, such as scFv antibodies, capable of specifically binding to cell surface antigens. The methods of the invention generally comprise contacting labeled antigen-expressing cells with labeled immunobinder-expressing cells and isolating immunobinder-expressing cells that bind to the antigen-expressing cells using a cell sorter. These methods are particularly useful for the rapid and efficient identification of immunobinders against conformational epitopes present in integral membrane proteins, such as GPCRs. The invention also provides isolated immunobinders and immunobinder-encoding nucleic acids identified using the methods of the invention.

In one aspect the invention provides a method for identifying an immunobinder that specifically binds to a cell surface antigen of interest. The method comprises: providing a plurality of immunobinder-expressing cells operably linked to a first sortable label; providing a plurality of antigen-expressing cells operably linked to a second sortable label, wherein the antigen of interest is displayed at the surface of the antigen expressing cell; contacting the antigen-expressing cells with the immunobinder-expressing cells; and separating from the plurality of immunobinder-expressing cells, one or more immunobinder-expressing cells that can specifically bind to the antigen-expressing cells using a cell sorter (e.g., a fluorescence activated cell sorter), wherein the presence of the first and second sortable label in a single cellular complex (e.g., a complex formed between an antigen and a B-cell receptor) is indicative of the binding of an immunobinder-expressing cell to an antigen-expressing cell, thereby identifying an immunobinder that binds to an antigen of interest.

In some embodiments, the separated immunobinder-expressing cells are clonally isolated.

In certain embodiments, the clonally isolated immunobinder-expressing cells are subjected to clonal expansion using methods well-known to those of skill in the art.

In other embodiments, the immunobinder-encoding nucleic acid sequence is isolated from immunobinder-expressing cells. Isolation of the nucleic acid sequence can occur after clonal isolation or after clonal expansion. Suitable methods for isolation of the immunobinder-encoding nucleic acid sequence include PCR, e.g., single-cell PCR.

In some embodiments, immunobinder-expressing cells isolated using the methods of the invention are subject to a cell-based assays in order to functionally characterize the immunobinder. Suitable cell-based assays include CELISA.

In some embodiments, the immunobinder is an antibody. Such antibodies include, mouse, rabbit, rabbitized, chicken, camel, camelized, human, humanized and chimeric antibodies. Suitable antibody formats include, without limitation, Fab, Dab, Nanobody and scFv.

In some embodiments, the antigen of interest is expressed from an exogenous gene. In other embodiments, the antigen of interest is a genetically engineered antigen. In other embodiments, the antigen of interest is an integral membrane protein. Suitable integral membrane proteins include, without limitation, G protein-coupled receptors (GPCRs, such as CXCR2) or ion channels.

In some embodiments, the first or second sortable label is a fluorescent label. Suitable fluorescent labels include, without limitation, fluorescent proteins, antibody/fluor conjugates and fluorescent cellular labels.

In some embodiments, the antigen-expressing cells are yeast or mammalian cells (e.g., human cells). In some embodiments, the antigen-expressing cells express an exogenous antigen. In some embodiments the antigen-expressing cells are transfected with an expression vector.

In some embodiments, the immunobinder-expressing cells are yeast or mammalian cells. Suitable mammalian cells include, without limitation, B-cells, e.g., rabbit B-cells. In some embodiments the B-cells are isolated from an immunized animal, e.g., an animal immunized by DNA vaccination. In some embodiments, the immunobinder-expressing cells comprise an immunobinder expressed from an expression vector.

In another aspect, the invention provides an isolated nucleic acid molecule encoding an immunobinder identified by the methods of the invention.

In another aspect, the invention provides a method of producing an immunobinder capable of binding to an antigen of interest, comprising introducing an immunobinder-encoding nucleic acid sequence identified by the methods of the invention into an expression environment such that the encoded immunobinder is produced.

In another aspect, the invention provides an immunobinder produced by the methods of the invention.

In another aspect, the invention also provides a method for identifying a B-cell clone that specifically binds to a cell surface antigen of interest comprising: immunizing an animal with DNA encoding a cell surface antigen; isolating B-cells from the immunized animal; labeling the B-cells with a first sortable label; providing a plurality of antigen-expressing cells operably linked to a second sortable label, wherein the antigen of interest is displayed at the surface of the antigen expressing cell; contacting the antigen-expressing cells with the B-cells; and separating from the plurality of B-cells, one or more B-cells that can specifically bind to the antigen-expressing cells using a cell sorter, wherein the presence of the first and second sortable label in a single cellular complex is indicative of the binding of an B-cell to an antigen-expressing cell, thereby identifying a B-cell clone that binds to a antigen of interest.

DEFINITIONS

In order that the present invention may be more readily understood, certain terms will be defined as follows. Additional definitions are set forth throughout the detailed description.

The term "antibody" refers to whole antibodies and any antigen binding fragment (i.e., "antigen-binding portion," "antigen binding polypeptide," or "immunobinder") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "chimeric antibody" refers to an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "antigen-binding portion" of an antibody (or simply "antibody portion") refers to one or more fragments of an antibody that retain the ability to specifically bind to an antigen (e.g., TNF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a single domain such as a dAb fragment (Ward et al., (1989) Nature 341:544-546), which consists of a VH domain; and (vi) an isolated complementarity determining region (CDR) or (vii) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the VH and CH1 domains; (v) a Fv fragment consisting of the VL and VH domains of a single arm of an antibody, (vi) a single domain antibody such as a Dab fragment (Ward et al., (1989) Nature 341:544-546), which consists of a VH or VL domain, a Camelid (see Hamers-Casterman, et al., Nature 363:446-448 (1993), and Dumoulin, et al., Protein Science 11:500-515 (2002)) or a Shark antibody (e.g., shark Ig-NARs Nanobodies®; and (vii) a nanobody, a heavy chain variable region containing a single variable domain and two constant domains.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is improved stability (e.g., thermal stability). In another embodiment, the functional property is improved solubility (e.g., under cellular conditions). In yet another embodiment, the functional property is non-aggregation. In still another embodiment, the functional property is an improvement in expression (e.g., in a prokaryotic cell). In yet another embodiment the functional property is an improvement in refolding yield following an inclusion body purification process. In certain embodiments, the functional property is not an improvement in antigen binding affinity.

The term "frameworks" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface. Such frameworks can also be referred to as scaffolds as they provide support for the presentation of the more divergent CDRs. Other CDRs and frameworks of the immunoglobulin superfamily, such as ankyrin repeats and fibronectin, can be used as antigen binding molecules (see also, for example, U.S. Pat. Nos. 6,300,064, 6,815,540 and U.S. Pub. No. 20040132028).

The term "epitope" or "antigenic determinant" refers to a site on an antigen to which an immunoglobulin or antibody specifically binds. An epitope typically includes at least 3, 4, 5, 6, 7, 8, 9, 10, 11, 12, 13, 14 or 15 amino acids in a unique spatial conformation. See, e.g., Epitope Mapping Protocols in Methods in Molecular Biology, Vol. 66, G. E. Morris, Ed. (1996).

The terms "specific binding", "selective binding", "selectively binds", and "specifically binds" refer to antibody binding to an epitope on a predetermined antigen. Typically, the antibody binds with an affinity (K) of approximately less than $10^{-7}$ M, such as approximately less than $10^{-8}$ M, $10^{-9}$ M or $10^{-10}$ M or even lower.

The term "$K_D$," refers to the dissociation equilibrium constant of a particular antibody-antigen interaction. Typically, the antibodies of the invention bind to an antigen with a dissociation equilibrium constant ($K_D$) of less than approximately 10-7 M, such as less than approximately $10^{-8}$ M, $10^{-9}$ M or $10^{-10}$ M or even lower, for example, as determined using surface plasmon resonance (SPR) technology in a BIACORE instrument.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared×100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment can be provided using, for instance, the method of Needleman et al. (1970) J. Mol. Biol. 48: 443-453, implemented conveniently by computer programs such as the Align program (DNAstar, Inc.). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared× 100. For instance, if 6 of 10 of the positions in two sequences are matched and 2 of 10 positions contain conservative substitutions, then the two sequences have 80% positive similarity.

As used herein, the term "conservative sequence modifications" is intended to refer to amino acid modifications that do not negatively affect or alter the binding characteristics of the antibody containing the amino acid sequence. Such conservative sequence modifications include nucleotide and amino acid substitutions, additions and deletions. For example, modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue may be replaced with another amino acid residue from the same side chain family. Methods of identifying nucleotide and amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

"Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability can be exhibited at the single residue level, multiple residue level, multiple residue with gaps, etc. Residues can exhibit conservation of the identical residue or can be conserved at the class level. Examples of amino acid classes include polar but uncharged R groups (Serine, Threonine, Asparagine and Glutamine); positively charged R groups (Lysine, Arginine, and Histidine); negatively charged R groups (Glutamic acid and Aspartic acid); hydrophobic R groups (Alanine, Isoleucine, Leucine, Methionine, Phenylalanine, Tryptophan, Valine and Tyrosine); and special amino acids (Cysteine, Glycine and Proline). Other classes are known to one of skill in the art and may be defined using structural determinations or other data to assess substitutability. In that sense, a substitutable amino acid can refer to any amino acid which can be substituted and maintain functional conservation at that position.

It will be recognized, however, that amino acids of the same class may vary in degree by their biophysical properties. For example, it will be recognized that certain hydrophobic R groups (e.g., Alanine,) are more hydrophilic (i.e., of higher hydrophilicity or lower hydrophobicity) than other hydrophobic R groups (e.g., Valine or Leucine). Relative hydrophilicity or hydrophobicity can be determined using art-recognized methods (see, e.g., Rose et al., Science, 229: 834-838 (1985) and Corvette et al., J. Mol. Biol., 195: 659-685 (1987)).

As used herein, when one amino acid sequence (e.g., a first VH or VL sequence) is aligned with one or more additional amino acid sequences (e.g., one or more VH or VL sequences in a database), an amino acid position in one sequence (e.g., the first VH or VL sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

The term "nucleic acid molecule," refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector," refers to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

The term "host cell" refers to a cell into which an expression vector has been introduced. Host cells can include bacterial, microbial, plant or animal cells. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. Suitable microbes include *Saccharomyces cerevisiae* and *Pichia pastoris*. Suitable animal host cell lines include CHO (Chinese Hamster Ovary lines) and NS0 cells.

The terms "treat," "treating," and "treatment," refer to therapeutic or preventative measures described herein. The methods of "treatment" employ administration to a subject, in need of such treatment, an antibody of the present invention, for example, a subject having a GPCR-mediated disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" refers to an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "subject" refers to any human or non-human animal. For example, the methods and compositions of the present invention can be used to treat a subject with a GPCR-mediated disorder.

The term "rabbit" as used herein refers to an animal belonging to the family of the leporidae.

The term "cell sorter" refers to any means for separating cells based upon the presence of a detectable "sortable" label. Such means include, without limitation, a fluorescence activation cell sorter. Any cellular labels can be used as sortable labels including, without limitation, fluorescent proteins, e.g. Green fluorescent protein, antibody/fluor conjugates and fluorescent cellular labels, e.g., fluorescent calcium ionophores The term "cellular complex" refers to a one or more antigen-expressing cells bound to one or more immunobinder-expressing cells, wherein the binding is mediated by the antigen on the surface of the antigen-expressing cell. In some embodiments, the binding of an antigen-expressing cell to an immunobinder-expressing cell consists of a direct interaction between the antigen on the surface of the antigen-expressing cell and the immunobinder on the surface of the immunobinder-expressing cell.

The term "clonally isolating" refers to any means for the isolation of individual cell clones from a cell population. Suitable means include, without limitation, the limiting dilution and transfer of cells to multiwell plates such that each well contains no more than a single cell.

The term "obtaining the immunobinder-encoding nucleic acid sequence" refers to any means for obtaining the nucleic acid sequence of an immunobinder expressed by an immunobinder-expressing cell. Suitable means include, without limitation, nucleic acid isolation, PCR amplification and DNA sequencing of the immunobinder-encoding nucleic acid sequence from the immunobinder-expressing cell. In some embodiments, immunobinder-encoding nucleic acid sequences are amplified by PCR from single cells, i.e. "single cell PCR".

The term "exogenous antigen" refers to an antigen not normally expressed in a particular host cell. For example, an exogenous antigen can be from a different kingdom, phylum class, order, genus or species from the host cell, e.g., a human antigen expressed in a yeast cell. Additionally or alternatively, an exogenous antigen can be from the same species but inappropriately expressed in that host cell, e.g, a lung specific antigen expressed in a brain cell. "Exogenous antigen" also refers to mutant an antigen not normally found in a normal cell, e.g., a cancer specific mutant antigen expressed in a lung cell.

The term "genetically engineered antigen" refers to any antigen that has been produced by recombination DNA techniques and includes antigens that are chimeras or contain point mutation, deletions and/or insertions. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending of the specific embodiment, selected definitions, embodiments or ranges may not apply.

The present invention provides a screening method using FACS to identify and separate immunobinder-expressing cells in adherence with cells expressing corresponding antigen. In particular embodiments, the immunobinder is an antibody.

Antigen Expression

The target antigen for antibody preparation can be any protein, peptide, nucleotide, carbohydrate, lipid, and other molecules that are soluble or expressed on a cell surface or integrated in the plasma membrane. Antigens can be native or synthetic. Preferably, a target antigen is a protein or peptide. Non-limiting examples of a target antigen include CXCR1, CXCR2, CXCR3, CXCR4, CXCR5, CXCR6, CCR1, CCR2, CCR3, CCR4, CCR5, CCR6, CCR8, CFTR, CIC-1, CIC-2, CIC-4, CIC-5, CIC-7, CIC-Ka, CIC-Kb, Bestrophins, TMEM16A, GABA receptor, glycin receptor, ABC transporters, NAV1.1, NAV1.2, NAV1.3, NAV1.4, NAV1.5, NAV1.6, NAV1.7, NAV1.8, NAV1.9, sphingosin-1-phosphate receptor (S1P1R), NMDA channel etc. In one embodiment, the target antigen is a transmembrane protein. In another embodiment, the target antigen is a multispan transmembrane protein, for example, G protein coupled receptors (GPCRs), ion channels, etc.

The family of GPCRs has at least 250 members (Strader et al. FASEB J., 9:745-754, 1995; Strader et al. Annu Rev. Biochem., 63:101-32, 1994). It has been estimated that one percent of human genes may encode GPCRs. GPCRs bind to a wide-variety of ligands ranging from photons, small biogenic amines (i.e., epinephrine and histamine), peptides (i.e., IL-8), to large glycoprotein hormones (i.e., parathyroid hormone). Upon ligand binding, GPCRs regulate intracellular signaling pathways by activating guanine nucleotide-binding proteins (G proteins). Interestingly, GPCRs have functional homologues in human cytomegalovirus and herpesvirus, suggesting that GPCRs may have been acquired during evolution for viral pathogenesis (Strader et al., FASEB J., 9:745-754, 1995; Arvanitakis et al. Nature, 385:347-350, 1997; Murphy, Annu Rev. Immunol. 12:593-633, 1994).

The characteristic feature of most GPCRs which have been known up to now is that seven clusters of hydrophobic amino acid residues are located in the primary structure and pass through (span) the cell membrane at each region thereof. The domains are believed to represent transmembrane alpha-helices connected by three intracellular loops, three extracellular loops, and amino- and carboxyl-terminal domains (K. Palczewski et al., Science 289, 739-45 (2000)). Most GPCRs have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. It is well known that these structures detailed above are common among G protein coupled receptor proteins and that the amino acid sequences corresponding to the area where the protein passes through the membrane (membrane-spanning region or transmembrane region) and the amino acid sequences near the membrane-spanning region are often highly conserved among the receptors. Thus, due to the high degree of homology in GPCRs, the identification of novel GPCRs, as well as identification of both the intracellular and the extracellular portions of such novel members, is readily accomplished by those of skill in the art. By way of example, the book of Watson and Arkinstall (1994), incorporated herein by reference, provides the sequences of over 50 GPCRs. The book further describes, for each sequence, the precise residues comprising each of the transmembrane domains.

The binding sites for small ligands of G-protein coupled receptors are believed to comprise a hydrophilic socket located near the extracellular surface and formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding. The ligand binding site for peptide hormones receptors and receptors with other larger ligands such as glycoproteins (LH, FSH, hCG, TSH), and the Ca2+/glutamate/GABA classes of receptors likely residue in the extracellular domains and loops.

A key event for the switch from inactive to active receptor is ligand-induced conformational changes of transmembrane helices 3 (TM3) and 6 (TM6) of the GPCRs that have 7 transmembrane spanning helices (U. Gether, and B. K. Kolbilka, J. Biol. Chem. 273, 17979-17982 (1998)). These helical movements in turn alter the conformation of the intracellular loops of the receptor to promote activation of associated heterotrimeric G proteins. Mutagenesis studies (S. Cotecchia, J. Ostrowski, M. A. Kjelsberg, M. G. Caron and R. J. Lefkowitz, J. Biol. Chem. 267, 1633-1639 (1992); E. Kostenis, B. R. Conklin and J. Wess, Biochemistry 36, 1487-1495 (1997); M. A. Kjelsberg, S. Coteechia, J. Ostrowski, M. G. Caron, and R. J. Lefkowitz, J. Biol. Chem. 267, 1430-1433 (1992)) demonstrated that the third intracellular loop (i3) mediates a large part of the coupling between receptor and G protein. I3 loops expressed as minigenes have also been shown to directly compete with adrenergic receptors for Gq binding (L. M. Luttrell, J. Ostrowski, S. Cotecchia, H. Kendal and R. J. Lefkowitz, Science 259, 1453-1457 (1993)), or can activate G proteins as soluble peptides in cell-free conditions (T. Okamoto et al., Cell 67, 723-730 (1991)).

The antigen of interest can be of endogenous source in the target cell (sometimes also referred to as antigen-expressing cell). Alternatively, exogenous molecules can be introduced into cells to express the antigen. The introduction of the antigen into cells can be practiced by any method known to a person with ordinary skills in the art. In one embodiment, a polynucleotide encoding the antigen as a polypeptide can be inserted in vitro into a vector, which can further be introduced into target cells for expression. The polynucleotide can contain the cDNA sequence, DNA sequence, or other sequences known in the art, of the target antigen. The vector can be plasmid, cosmid, liposome, or other natural or artificial vectors known in the art. The introduction can be a process of transfection, transformation, infection, direct micro-injection of materials, biolistic particle delivery, electroporation, or other methods known in the art. The target cell expressing the antigen can be any cells known in the art, including, for example, cells directly taken from animals, e.g., cancer cells, non-cancer cells, primary cells, etc., or cells with molecular engineering, e.g., culture cells (e.g., Chinese Hamster Ovary (CHO) cells, HEK293 cells, etc.), immortalized cells, transfected/infected cells, T cells, etc. Alternatively, the target cell can come from non-animal sources, e.g., bacterial, insect, etc. In one embodiment, the cells expressing the target antigen are yeast cells, preferably yeast spheroblasts. Alternatively, the target "cell" can be an artificial cell-like body or structure, e.g., liposome, single-layer membrane body, etc. The expression of the antigen in the target cell or cell-like bodies can be transient, i.e., the expression will attenuate or stop after a comparatively short period of time (e.g., from minutes to several days), or stable, i.e., the expression will sustain at a comparatively stable level for a comparatively long time (e.g., after several days or several generations of cells). In one preferable embodiment, the antigen is expressed on the extracellular surface of the plasma membrane of the target cell. In another preferable embodiment, the antigen is an integral or multispan membrane antigen. To get to its location on the plasma membrane, the antigen can be expressed directly on these locations, or can be translocated to these locations after their expression in the cytoplasm of the target cell. This translocation can be a natural process of the target cell or an engineered process by, for example, attaching a signal/tag molecule (e.g., Golgi sorting signals, antibodies to certain membrane-bound molecules, etc.), anchoring graft (e.g., a glycosylphosphatidylinositol (GPI) anchor), or chemical crosslink to the antigen, mutating the antigen, or other methods known in the art, before or after the antigen expression, which leads to its translocation.

Immunobinder-Expressing Cells and Immunization

In one embodiment, the immunobinder-expressing cells to be selected by the method described herein are mammalian B cells, preferably rabbit B-cells.

In a preferred embodiment, the B cells originate from an animal that was immunized with the target of interest. The immunization of the animal can be practiced by any method known to a person with ordinary skills in the art. Typically, the B-cells are isolated from lymphatic organs of an immunized animal (such as spleen or lymph nodes).

In one preferred embodiment, the immunization of antigen of the interest is done by DNA immunization/vaccination. Alternatively, cells expressing the target antigen are injected into animals (e.g., rabbit, rat, mouse, hamster, sheep, goat, chicken, etc.) for the immunization. The preferred animal for this immunization step is a rabbit. DNA immunization/vaccination induces a rapid immune response and allows for native expression, and usually only native expression, of target antigens. Because it does not involve the expression and handling of recombinant proteins, this process is more efficient and cost-effective than traditional immunization with recombinant proteins. In addition, more importantly, the in vivo expressed antigen possesses the same secondary structures and may even possess the same post-translational modifications as the target protein in its natural context, which improves the correctness of recognition by the prepared antibodies against the target antigen. An exemplary DNA immunization is illustrated in a Canadian patent application CA2350078 and in WO04/087216. Specifically, the DNA encoding the polypeptide as the target antigen is introduced directly into an animal through a gene gun method, resulting in expression of a polypeptide in the animal, which expression causes the formation of antibodies against the polypeptide. In order to achieve a more vigorous antibody formation, so-called genetic adjuvants are applied simultaneously with the polypeptide-encoding DNA. These genetic adjuvants are plasmids which express cytokines (e.g., GM-CSF, IL-4 and IL-10) and which stimulate the humoral immune response in the laboratory animals. In one preferred embodiment, the antibody to the target antigen is expressed on the cell surface of B cells as a B cell receptor (BCR). In another preferred embodiment, the antibody-expressing cell is a memory B cell, characterized and distinguishable from regular B cells by the absence of any IgM on its surface.

In one embodiment, the immunobinder-expressing cells are yeast cells and the immunobinders are preferably antibody fragments, more preferably scFv.

Screening Using Fluorescent-Activated Cell Sorting (FACS)

After the immunization step, the membrane-bound antibody on B cells that specifically binds to the target antigen need to be separated from other cells expressing non-specific antibodies. In one preferred embodiment, through the antigen-antibody binding, B cells expressing the specific antibody on its plasma membrane is adhered to the target cells expressing the antigen. In another one preferred embodiment, other or more interactions (e.g., same or different antigen-antibody interactions, chemical crosslinks, ligand-receptor interactions, etc.) may occur between B cells and target cells. The B cells can be in a pool of B cells expressing different antibodies, or in combination with other immune cells, collected directly from the immunized animal, from a pool of immunized/non-immunized animals, or from in vitro engineering processes, for example, a library of B cells expressing different antibodies by V(D)J genetic recombination technique.

The separation of the B cells expressing antibodies specific to the target antigen can be done in any method known in the art. These include, but are not limited to, panning on antigen, limited dilution, affinity purification, or other methods utilizing the characteristics of the expressed antibodies or the antibody-producing B cells.

In one preferred embodiment, the antigen-expressing cells are labeled with a tag useful for future detection and/or isolation of the adhered B cells. The tag can be a crosslinker, antigen/antibody, small molecules (e.g., glutathione (GSH), biotin/avidin, etc.), magnetic particles, fluorescence tag, etc. In one preferred embodiment, the antigen-expressing cells are labeled with a fluorescent protein/peptide. In another embodiment, the antibody-producing B cells are also labeled with a tag, preferably, a different fluorescent protein/peptide. In yet another embodiment, the B cells in adherence to the antigen-expressing cells can be detected by the emission of fluorescence from the fluorescent protein/peptide labeled on B cells. In still another embodiment, the B cell and the antigen-expressing cell in adherence can be detected by the emission of fluorescence from two different fluorescent protein/peptide labeled on them. In one preferred embodiment, B cells expressing antibodies specific to the target antigen can be detected and further separated from other antibody-producing B cells by the emission of both fluorescence from fluorescent proteins/peptides labeled on them and on adhered APCs. Preferably, this detection and separation can be performed by fluorescence-activated cell sorting (FACS) technique.

The acronym FACS is trademarked and owned by Becton Dickinson (Franklin Lakes, N.J.). As used herein, the term FACS shall represent any form of flow cytometry based cell sorting.

Fluorescence-activated cell sorting is a specialized type of flow cytometry. It provides a method for sorting a heterogeneous mixture of biological cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In a typical FACS system, the cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Just before the stream breaks into droplets the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement and the opposite charge is trapped on the droplet as it breaks from the stream. The charged droplets then fall through an electrostatic deflection system that diverts droplets into containers based upon their charge. In some systems the charge is applied directly to the stream and the droplet breaking off retains charge of the same sign as the stream. The stream is then returned to neutral after the droplet breaks off.

The fluorescent labels for FACS technique depend on the lamp or laser used to excite the fluorochromes and on the detectors available. The most commonly available lasers on single laser machines are blue argon lasers (488 nm). Fluorescent labels workable for this kind of lasers include, but not limited to, 1) for green fluorescence (usually labelled FL1): FITC, Alexa Fluor 488, GFP, CFSE, CFDA-SE, and DyLight 488; 2) for orange fluorescence (usually FL2): PE, and PI; 3) for red fluorescence (usually FL3): PerCP, PE-Alexa Fluor 700, PE-Cy5 (TRI-COLOR), and PE-Cy5.5; and 4) for infrared fluorescence (usually FL4; in some FACS machines): PE-Alexa Fluor 750, and PE-Cy7. Other lasers and their corresponding fluorescent labels include, but are not limited to, 1) red diode lasers (635 nm): Allophycocyanin (APC), APC-Cy7, Alexa Fluor 700, Cy5, and Draq-5; and 2) violet lasers (405 nm): Pacific Orange, Amine Aqua, Pacific Blue, 4',6-diamidino-2-phenylindole (DAPI), and Alexa Fluor 405.

In a preferred embodiment, B cells are stained with labeled anti-IgG and anti-IgM antibodies and the memory B cells only being positively stained with the anti-IgG antibodies but not with the anti-IgM antibodies are preferentially selected. IgG have generally a higher affinity than IgM; positive B-cells expressing IgG but not IgM on their surface (which is characteristic for memory B-cells) are thereby selected. For said purpose, multicolor staining is preferably used, where antibodies specific for IgG and IgM are differentially labeled, e.g. with APC and FITC, respectively. Preferably, the target antigen and/or the target cell expressing the target antigen are also labeled. In one embodiment, the target antigen is stained indirectly by staining the cell that expresses the target antigen with an intracellular fluorescent dye.

The present invention provides a method using FACS to screen B cells pools, in which B cells may adhere to cells expressing target antigens, to identify and further isolate B cells producing antibodies specifically binding to the target antigen of interest. Preferably, the B cells are labeled with a fluorescent label and the cells expressing the target antigen are separately labeled with a different fluorescent label. These labels can be either intracellular, extracellular, or integrated in the plasma membrane. After the immunization and production of antibodies, all B cells are pooled together and run through a FACS system. Only those B cells producing antibodies specific to the target antigen will adhere to the antigen-expressing cells. Their adherence shortens the distance between these two cells in the flow, compared to the large separation between other individual cells, leading to a "bi-color event" detectable during their concurrent passing through the scanning laser beam. Thus, the B cells producing antibodies of interest can be identified and then sorted into a different collection tube from other non-specific B cells.

In another preferred embodiment, if the interaction between the B cell and the corresponding antigen-expressing cell leads to certain modification of cellular characteristics, e.g., depolarization, fluorescence resonance energy transfer (FRET), etc., more fluorescent labels can be added to the cell capable of such modification. Thus, B cells and antigen-expressing cells in contact will give out a "tri-color" event or an event containing even more than three colors at the same time.

Alternatively, the identification and sorting of B cells in adherence does not require the existence of its fluorescent label. In one embodiment, the cell-cell interaction leads to functional changes in either cell. In another embodiment, these functional changes can be used to identify and further separate B cells producing antibodies specifically binding to the target antigen. For example, the cell-cell interaction may functionally block or activate receptor signaling in either cell, leading to cellular changes, e.g., the $Ca^{2+}$ efflux changes, etc., detectable by the FACS system. Thus, by monitoring these detectable functional changes, B cells of interest can also be identified and separated. One particular embodiment of functionally blocking or activating receptor signaling includes incubating B-cells with cells that functionally express a GPCR (G protein-coupled receptor). An agonist that signals through a GPCR can be added to the mixture to induce GPDR mediated $Ca^{2+}$ efflux from the endoplasmatic reticulum. In case an antibody presented on a B-cell would functionally block agonist signaling, $Ca^{2+}$ efflux would consequently also be blocked by this cell-cell interaction. $Ca^{2+}$ efflux can e.g. be quantitatively measured by flow-cytometry. Therefore, only B-cell/target cell conglomerates that either show increase or decrease in $Ca^{2+}$ efflux would be sorted.

Affinity Assays to Antibodies Produced by the Isolated B Cells

In certain embodiments, B-cells are cultivated under suitable conditions so that antibodies are secreted into the culture medium. The produced antibodies are, for example, monoclonal antibodies. The cultivation may involve the use of a helper cell line, such as a thymoma helper cell line (e.g. EL4-B5, see Zubler et al, 1985, J. Immunol., 134(6): 3662-3668).

Optionally, additional affinity assays can be performed before further processing to evaluate the selectivity and the ability to compete with the ligand of antibodies produced by the isolated B cells. These assays include, but are not limited to, cell-based assays (e.g., cell ELISA (CELISA), which is a modified ELISA process in which entire cells are used for coating). As discussed in CA2350078, CELISA can be conducted as described below in Examples. The validation step is performed to test the generated antibodies for specific binding to the target, e.g. for excluding antibodies which are directed against a protein being expressed on the cell surface other than the target protein.

Alternatively, the identified and isolated B cells of interest can be directly examined for antibody affinity and the B cells can be separated from adhered antigen-expressing cells before the processing Further Processing of Isolated B Cells for Antibody Production The identified and isolated B cells, optionally tested by affinity assay (e.g., CELISA), can be further processed to produce immunobinders of interest. Traditional hybridoma technique, for example, can be used. This may involve steps such as purifying the immunobinders, elucidating their amino acid sequence and/or nucleic acid sequence.

Alternatively, characterization of the binders is performed in their scFv format. For this approach CDR sequences of binders expressed on sorted B-cells would be retrieved by RT-PCR from either the cultured sorted cells or from single cells directly. Combination of two pools of partially overlapping oligonucleotides in which one oligonucleotide pool is coding for the CDRs and a second pool encodes the framework regions of a suitable scFv scaffold would allow for generation of a humanized scFv in a one-step PCR procedure. HT sequencing, cloning and production would allow to perform clone selection based on the performance of the purified humanized scFv, instead of characterizing secreted IgG in the cell culture supernatant. A scFv scaffold suitable to accept CDRs from any rabbit antibody has been identified and characterized ("rabbitized" human FW or rabbit acceptor RabTor; see WO09/155726, which is hereby incorporated by reference in its entirety). The proof of concept for a variety of CDRs that in some cases even contain the rabbit specific inter-CDR disulfide bonds has been shown.

A general description of making rabbitized antibody is described below.

Grafting of Immunobinders

The antigen binding regions or CDRs of immunobinders identified using the methods of the invention can be grafted into acceptor antibody frameworks. Such grafting can, for example, reduce the immunogenicity of the immunobinder or improve its functional properties, e.g., improve thermodynamic stability.

General methods for grafting CDRs into human acceptor frameworks have been disclosed by Winter in U.S. Pat. No. 5,225,539, which is hereby incorporated by reference in its entirety.

Specific strategies for grafting CDRs from rabbit monoclonal antibodies are disclosed in U.S. Provisional Patent Application Nos. 61/075,697, and 61/155,041, which are hereby incorporated by reference in their entirety. These strategies are related to that of Winter but diverge in that the acceptor antibody frameworks are particularly suitable as universal acceptor for all human or non-human donor antibodies. In particular, the human single-chain framework FW1.4 (a combination of SEQ ID NO: 1 (named a43 in WO03/097697) and SEQ ID NO: 2 (named KI27 in WO03/097697)) has been shown to be highly compatible with the antigen-binding sites of rabbit antibodies. Therefore, the FW1.4 represents a suitable scaffold to construct stable humanized scFv antibody fragments derived from grafting of rabbit loops.

Moreover, it was found that FW1.4 could be optimized by substituting 5 or 6 residue positions in the heavy chain of FW1.4 and/or by substituting 1 position in the light chain of FW1.4. Thereby, it was surprisingly found that loop conformation of a large variety of rabbit CDRs in the VH could be fully maintained, largely independent of the sequence of the donor framework. Said 5 or 6 residues in the heavy chain as well as the 1 position in the light chain of FW1.4 are conserved in rabbit antibodies. The consensus residue for the 5 or 6 positions in the heavy chain, as well as the one position in the light chain, was deduced from the rabbit repertoire and introduced into the sequence of the human acceptor framework. As a result, the modified framework 1.4 (referred to therein as rFW1.4) is compatible with virtually any rabbit CDR. Contrary to the rabbit wild type single chains, rFW1.4 containing different rabbit CDRs is well expressed and almost fully retains the affinity of the original donor rabbit antibodies.

Accordingly, exemplary immunobinder acceptor frameworks comprise (i) a variable heavy chain framework having at least 70% identity, preferably at least 75%, 80%, 85%, 90%, more preferably at least 95% identity, to SEQ ID No. 1; and/or (ii) a variable light chain framework having at least 70% identity, preferably at least 75%, 80%, 85%, 90%, more preferably at least 95% identity, to SEQ ID No. 2.

In a preferred embodiment, the variable light chain comprises Threonine (T) at position 87 (AHo numbering).

In a preferred embodiment, said immunobinder acceptor framework comprises (i) a variable heavy chain framework selected from the group consisting of SEQ ID No. 1, SEQ ID No. 4 and SEQ ID No. 6; and/or (ii) a variable light chain framework of SEQ ID No. 2 or SEQ ID No. 9.

In a preferred embodiment, the variable heavy chain framework is linked to a variable light chain framework via a linker. The linker may be any suitable linker, for example a linker comprising 1 to 4 repeats of the sequence GGGGS (SEQ ID No. 10), preferably a (GGGGS)$_4$ peptide (SEQ ID No. 8), or a linker as disclosed in Alfthan et al. (1995) Protein Eng. 8:725-731.

In a most preferred embodiment, the immunobinder acceptor framework is a sequence having at least 70%, 75%, 80%, 85%, 90%, more preferably at least 95% identity, to SEQ ID.

No. 3. More preferably, the immunobinder acceptor framework comprises or is SEQ ID. No. 3.

In another preferred embodiment, the immunobinder acceptor framework is a sequence having at least 70%, 75%, 80%, 85%, 90% more preferably at least 95% identity, to SEQ ID No. 5. More preferably, the immunobinder acceptor framework comprises or is SEQ ID No. 5.

In another preferred embodiment, the immunobinder acceptor framework is a sequence having at least 70%, 75%, 80%, 85%, 90%, more preferably at least 95% identity, to SEQ ID No. 7. More preferably, the immunobinder acceptor framework comprises or is SEQ ID No. 7.

Furthermore, an exemplary variable heavy chain framework of SEQ ID No. 1 may be employed, further comprising one or more amino acid residues that generally support conformation of CDRs derived from a rabbit immunobinder. In particular, said residues are present at one or more amino acid positions selected from the group consisting of 24H, 25H, 56H, 82H, 84H, 89H and 108H (AHo numbering). These positions are proven to affect CDR conformation and are therefore contemplated for mutation to accommodate donor CDRs. Preferably, said one or more residues are selected from the group consisting of: Threonine (T) at position 24, Valine (V) at position 25 Glycine or Alanine (G/A) at position 56, Lysine (K) at position 82, Threonine (T) at position 84, Valine (V) at position 89 and Arginine (R) at position 108 (AHo numbering).

In a preferred embodiment, said variable heavy chain framework is or comprises SEQ ID No. 4 or SEQ ID No. 6. Both variable heavy chain frameworks may for example be combined with any suitable light chain framework.

The sequences disclosed above are the following (X residues are CDR insertion sites):

```
SEQ ID NO. 1:
variable heavy chain framework of FW1.4 (a43)
EVQLVESGGGLVQPGGSLRLSCAAS(X)_{n = 1-50}

WVRQAPGKGLEWVS(X)_{n = 1-50}

RFTISRDNSKNTLYLQMNSLRALDTAVYYCAK(X)_{n = 1-50}

WGQGTLVTVSS

SEQ ID NO. 2:
variable light chain framework of FW1.4 (K127)
LIVMTQSPSTLSASVGDRVIITC(X)_{n = 1-50}

WYQQKPGKAPKLLIY(X)_{n = 1-50}

GVPSRFSGSGSGALFTLTISSLQPDDFATYYC(X)_{n = 1-50}

FGQGTKILTVLG

SEQ ID NO. 3:
framework of FW1.4
LIVMTQSPSTLSASVGDRVIITC(X)_{n = 1-50}

WYQQKPGKAPKLLIY(X)_{n = 1-50}

GVPSRFSGSGSGALFTLTISSLQPDDFATYYC(X)_{n = 1-50}

FGQGTKILTVLGGGGSGGGGSGGGGSGGGGS EVQLVESGGGLVQPGGS

LRLSCAAS(X)_{n = 1-50}

WVRQAPGKGLLWVS(X)_{n = 1-50}

RFTISRDNSKNTLYLQMNSLRAEDTAVYYCAK(X)_{n = 1-50}

WGQGTLVTVSS

SEQ ID NO. 4:
variable heavy chain framework of rFW1.4
EVQLVESGGGLVQPGGSLRLSCTAS(X)_{n = 1-50}

WVRQAPGKGLLWVG(X)_{n = 1-50}

RFTISRDTSKNTVYLQMNSLRALDTAVYYCAR(X)_{n = 1-50}

WGQGTLVTYSS

SEQ ID NO. 5:
framework of rFW1.4
EIVMTQSPSTLSASVGDRVIITC(X)_{n = 1-50}

WYQQKPGKAPKLLIY(X)_{n = 1-50}

GVPSRFSGSGSGTEFTLTISSLQPDDFATYYC(X)_{n = 1-50}

FGQGTKILTVLGGGGGSGGGGSGGGGSGGGGSLVQLVLSGGGLVQPGGSL

RLSCTAS(X)_{n = 1-50}

WVRQAPGKGLLWVG(X)_{n = 1-50}

RFTISRDTSKNTVYLQMNSLRALDTAVYYCAR(X)_{n = 1-50}

WGQGTLVTVSS

SEQ ID NO. 6:
variable heavy chain framework of rFW1.4(V2)
EVQLVLSGGGLVQPGGSLRLSCTVS(X)_{n = 1-50}

WVRQAPGKGLLWVG(X)_{n = 1-50}

RFTISKDTSKNTVYLQMNSLRALDTAVYYCAR(X)_{n = 1-50}

WGQGTLVTVSS

SEQ ID NO. 7:
framework of rFW1.4(V2)
EIVMTQSPSTLSASVGDRVIITC(X)_{n = 1-50}

WYQQKPGKAPKLLIY(X)_{n = 1-50}

GVPSRFSGSGSGTEFTLTISSLQPDDFATYYC(X)_{n = 1-50}

FGQGTKILTVLGGGGGSGGGGSGGGGSGGGGS EVQLVLSGGGLVQPGGS

LRLSCTVS(X)_{n = 1-50}

WVRQAPGKGLLWVG(X)_{n = 1-50}

RFTISKDTSKNTVYLQMNSLRALDTAVYYCAR(X)_{n = 1-50}

WGQGTLVTVSS

SEQ ID NO. 8:
linker
GGGGSGGGGSGGGGSGGGGS

SEQ ID NO. 9:
substituted variable light chain framework of
FW1.4
EIVMTQSPSTLSASVGDRVIITC(X)_{n = 1-50}

WYQQKPGKAPKLLIY(X)_{n = 1-50}

GVPSRFSGSGSGTEFTLTISSLQPDDFATYYC(X)_{n = 1-50}

FGQGTKILTVLG
```

Thus, unlike the general method of Winter, the framework sequence used for the humanization methods of the invention is not necessarily the framework sequence which exhibits the greatest sequence similarity to the sequence of the non-human (e.g., rabbit) antibody from which the donor CDRs are derived. In addition, framework residue grafting from the donor sequence to support CDR conformation is not required.

The acceptor antibody frameworks can also comprise one or more of the stability enhancing mutations described in U.S.

Provisional Application Ser. No. 61/075,692, which is hereby incorporated by reference in its entirety. Exemplary solubility enhancing substitutions in the heavy chain framework are found at positions 12, 103 and 144 (AHo numbering). More preferably, the heavy chain framework comprises (a) Serine (S) at position 12; (b) Serine (S) or Threonine (T) at position 103 and/or (c) Serine (S) or Threonine (T) at position 144. Moreover, stability enhancing amino acids may be present at one or more positions 1, 3, 4, 10, 47, 57, 91 and 103 of the variable light chain framework (AHo numbering). More preferably, the variable light chain framework comprises glutamic acid (E) at position 1, valine (V) at position 3, leucine (L) at position 4, Serine (S) at position 10; Arginine (R) at position 47, Serine (S) at position 57, phenylalanine (F) at position 91 and/or Valine (V) at position 103.

EXAMPLES

Throughout the examples, the following materials and methods were used unless otherwise stated.
Materials and Methods In general, the practice of the present invention employs, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).
Cell ELISA (CELISA)

The following example describes the use of CELISA to analyze cells expressing CXCR2:

CHO cells expressing CXCR2 can be seeded at a density of 50,000 cells/well in 96-well half area plates. After overnight incubation at 37° C., cells can be fixed with 1% formaldehyde in PBS for 30 minutes at room temperature. Cell layers can be washed three times and non specific binding sites can be blocked with cell culture medium for one hour at room temperature. Next, after three washing steps, the supernatants can be diluted 1:1 in culture medium and added to the wells. In three control wells, a commercial rabbit anti-CXCR2 antibody can be spiked in supernatant. Supernatants can then be incubated on the cell layers for one and a half hours at room temperature. Finally, rabbit IgGs are detected with a goat anti-rabbit IgG Fc antibody coupled to HRP. Upon addition of a peroxidase substrate (Blue POD substrate from Roche), a colorimetric reaction would develop which could be stopped after 25 minutes with 1M HCl. Absorbance can be measured at 450 nm.

Example 1

B Cell Screening System Using Soluble Antigens

Figure 2A:
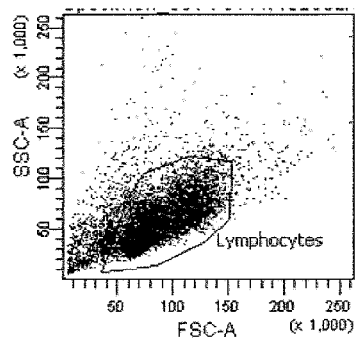
FIGS. 2A-2C: the FACS selection process of rabbit B cells binding to ESBA903 soluble target.
Figure 2B:
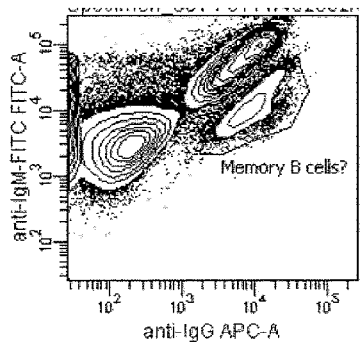
Figure 2C:
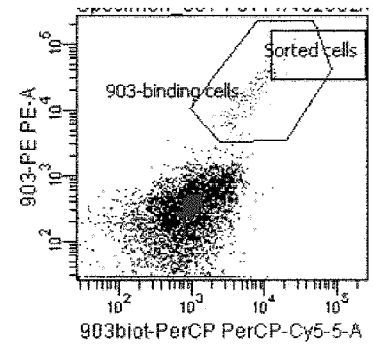

A FACS (fluorescence-activated cell sorting)-based screening system described in this invention is exemplified here capable of selecting B cells that bind to a target of interest, specifically, a soluble protein, via their B cell receptors (BCR). In this Example, the target was the single-chain anti-VEGF antibody ESBA903 labeled with a fluorescent dye (PE and PerCP). Lymphocyte suspension was prepared from the spleen of rabbits immunized with the recombinant target. Cells were then incubated with PE and PerCP labeled scFv as well as with antibodies specific for IgG (APC-labeled) or IgM (FITC labeled). ESBA903-positive B-cells that express IgG but not IgM on their surface were sorted and selected in 96-well plates (FIG. 2). As shown in panel A of FIG. 2, lymphocytes were gated according to forward and side scatter. Among them, IgG+ IgM− cells (probably memory B cells) were selected (panel B). Cells double-stained with scFv-PE and scFv-PerCP were expected to encode high affinity IgGs against the scFv (panel C). Cells showing the brightest fluorescence were sorted in 96-well plates with sorting statistics listed in panel D. By means of a thymoma helper cell line (EL4-B5: see Zubler et al, 1985, J. Immunol. 134(6): 3662-3668), selected B cells proliferated, differentiated into plasma cells and then secreted antibodies. The affinity of these IgG molecules for the target protein was verified by ELISA and Biacore measurements. Kinetic parameters are depicted in Table 1 for seven selected clones. These clones, from a pool of ~200 sorted cells, show high binding affinities in the low nanomolar to picomolar range. Finally, mRNAs for secreted IgG molecules were isolated from 6 clones of interest and the CDRs were grafted on ESBATech single-chain framework RabTor, also termed Framework rFW1.4.

TABLE 1

| Kinetic values for 7 B cell culture supernatants | | | |
|---|---|---|---|
| B-cell clone | ka [Ms$^{-1}$] | kd [s$^{-1}$] | $K_D$ [M] |
| SG2 | 2.91E+06 | 2.95E−04 | 1.01E−10 |
| SE11 | 3.63E+05 | 3.81E−04 | 1.05E−09 |
| 2E-03 | 8.34E+05 | 3.53E−04 | 4.23E−10 |
| 9E-03 | 8.66E+05 | 6.47E−04 | 7.47E−10 |
| 7D-03 | 3.97E+05 | 3.04E−04 | 7.65E−10 |
| 12B-02 | 1.08E+06 | 1.10E−04 | 1.01E−10 |
| 11G-02 | 5.48E+05 | 1.52E−04 | 2.78E−10 |

| Sorting statistics for FIG. 2. | | | |
|---|---|---|---|
| Population | #Events | % Parent | % Total |
| All Events | 100,000 | #### | 100.0 |
| Lymphocytes | 86,585 | 86.6 | 86.6 |
| Single Lymphocytes 1 | 86,013 | 99.3 | 86.0 |
| Single Lymphocytes 2 | 85,523 | 99.4 | 85.5 |
| Memory B cells? | 5,450 | 6.4 | 5.4 |
| Sorted Cells | 16 | 0.3 | 0.0 |
| 903-binding cells | 160 | 2.9 | 0.2 |

SELECTED LITERATURE

Zuber et al. Mutant EL-4 thymoma cells polyclonally activate murine and human B cells via direct cell interaction. J Immunol. 1985; 134(6):3662-3668.

Transmembrane Targets

The screening system described above works efficiently when the target is soluble, and when recombinant protein is available. However, some targets of interest are multispan transmembrane proteins (e.g., GPCRs and ion channels). Traditional immunization with recombinant protein is in these cases inadvisable or impossible. Further, FACS selection of B cells cannot be performed based on binding of purified, labeled proteins if the antigen is an integral membrane protein. In order to address these issues the following improvements of the above mentioned procedure were implemented.

1) Immunization with DNA Instead of Recombinant Protein:

DNA vaccination induces a rapid immune response against native antigen. Since no recombinant protein is needed, this technology is on one hand very cost-effective, on the other hand, and more importantly, this method allows for native expression of integral membrane complexes and/or multispan membrane proteins.

2) FACS Selection of B-Cells that Bind to Cells that Express an Integral Membrane Target Protein:

Flow cytometry normally measures the fluorescence emitted by single cells when they cross a laser beam. However, some researchers have already used cytometers to investigate cell-cell interactions, for example adhesion mediated by cadherins (Panorchan et al, 2006, J. Cell Science, 119, 66-74; Leong et Hibma, 2005, J. Immunol. Methods, 302, 116-124) or integrins (Gawaz et al, 1991, J. Clin. Invest, 88, 1128-1134). However, such studies did not demonstrate whether such cell-cell interactions will remain intact during the physical step of cell sorting. Furthermore, it has never been shown that the binding of a B cell receptor to its target being present on the surface of another cell will be strong enough to allow such physical sorting.

In order to select for B-cells that bind to transmembrane targets, cells (for example, CHO or HEK293 cells) can be transiently or preferentially stably transfected with the target of choice, or cells that naturally express the target of choice can be used. Such target cells are stained with an intracellular fluorescent dye (for example calcein) and incubated with the memory B lymphocytes of an immunized rabbit. B lymphocytes are stained with fluorescent antibodies binding to cell surface specific markers. Thus, selection of bi-color "events" consisting in two cells adhering to each other through BCR-target interactions (see FIG. 1) can be achieved.

The further processing of these B cells is performed as described above, which leads to the production of monoclonal antibodies, for example in the IgG or scFv format. To estimate the affinity of these antibodies for the target, CELISA (ELISA, where coating step is performed with entire cells) is being performed. With this method, the selectivity and the ability of antibodies to compete with the ligand can be evaluated. Finally, the CDRs of clones of interest will be cloned into our rabbitized framework (RabTor) by gene synthesis with the oligo extension method.

A read-out for B-cell sorting is not necessarily limited to cell-cell interaction, but can also be used to select for the ability of this interaction to functionally block/activate receptor signaling. For example, B-cells can be incubated with cells that functionally express a GPCR. An agonist that signals through a GPCR can be added to the mixture to induce GPCR mediated Ca2+ efflux from the endoplasmic reticulum. In case an antibody presented on a B-cell functionally blocks agonist signaling, Ca2+ efflux would consequently also be blocked by this cell-cell interaction. Ca2+ efflux can be quantitatively measured by flow-cytometry. Therefore only B-cell/target cell conglomerates that show no Ca2+ efflux would be sorted.

Example 2

Detection of the Interaction Between Beads Coated with Anti-TNFα Antibody and CHO Cells Expressing Membrane-Bound TNFα

Before a B cell screening against a transmembrane protein is initiated, it has to be demonstrated that cell-cell interactions (and especially interactions between BCR and transmembrane protein on target cell) can be positively selected with a FACS. To determine whether the high pressure in the flow-cytometry stream breaks non covalent binding between two cells, the following experiment was performed.

Figure 3:
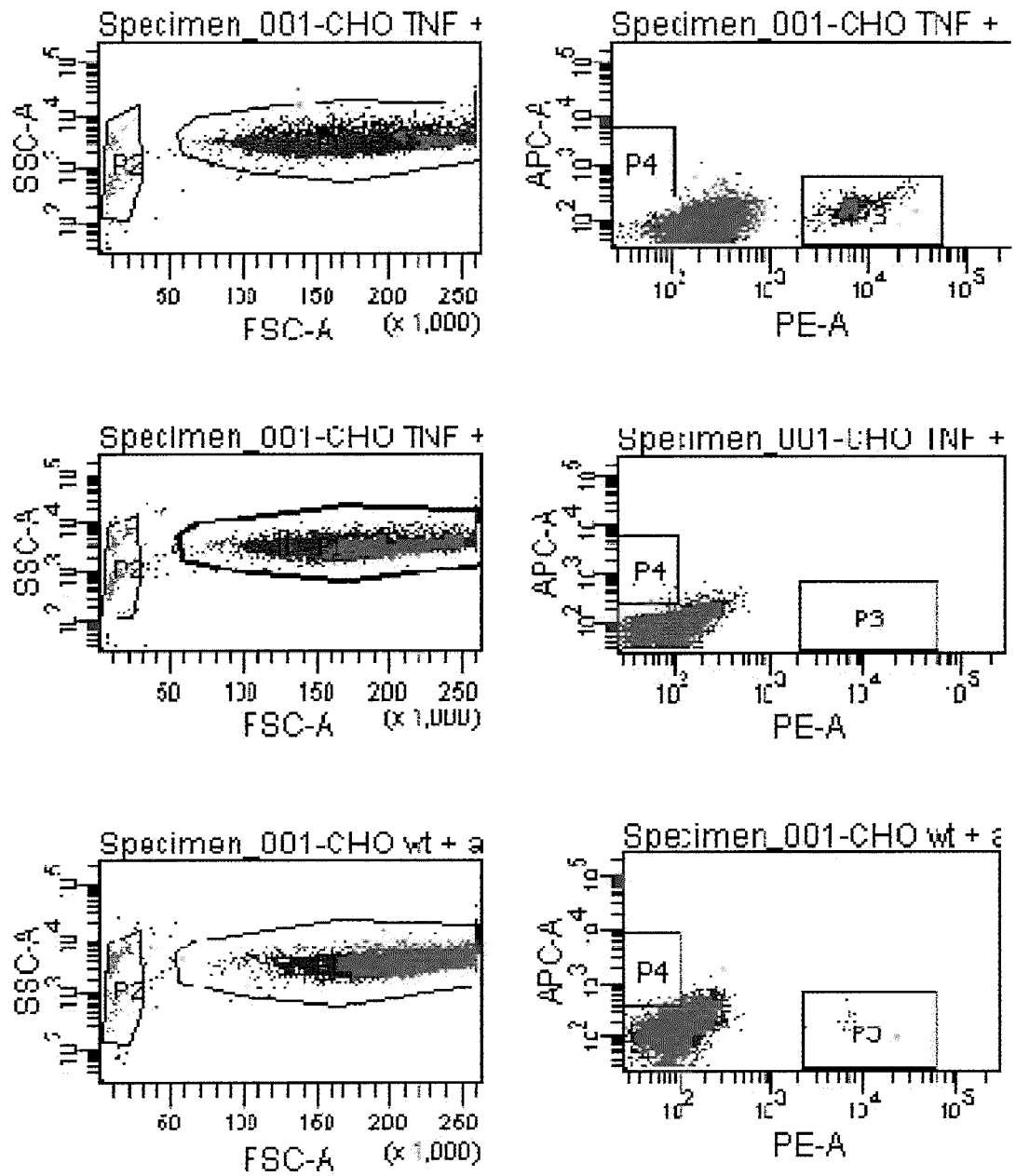
FIG. 3: Beads coated with anti-TNFalpha antibodies (PE labeled) bind to TNFalpha-transfected CHO cells (upper panel). Control beads coated anti-CD19 antibodies (APC labeled) did not bind TNFalpha transfected CHO cells (middle panel). Beads coated with anti-TNFalpha antibodies (PE labeled) did not bind to wildtype (wt) CHO cells (lower panel). Dot plots on the left show forward and side scatters, which indicate respectively the size and the granularity of the events. The single beads (~3 um) population was gated in P2. CHO cells eventually bound to beads (~30 um) were gated in P1. Dot plots in the middle show the P1 events (CHO cells) in respect to their PE or APC staining Thus, cells interacting with anti-TNFalpha beads would appear in P3 gate, and cells interacting with the anti-CD19 beads would appear in P4 gate. On the right, statistics for each sample are detailed.
Figure 4:
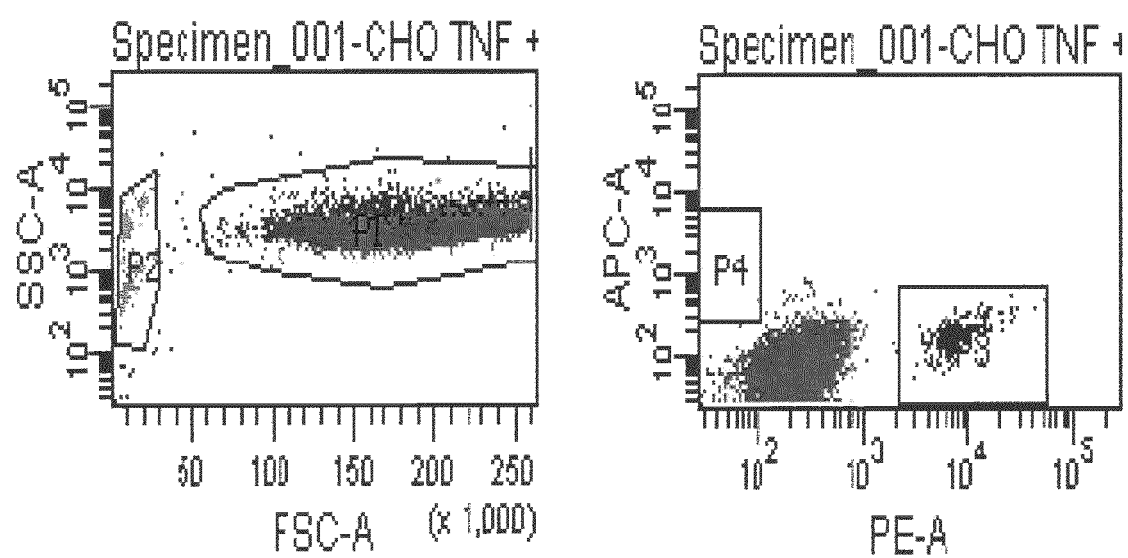
FIG. 4: Beads coated with anti-TNFalpha-PE and beads coated with anti-CD19-APC were mixed together with TNFalpha-transfected CHO cells. CHO cells were gated (P1), and among them cells binding to either anti-TNFalphaPE coated beads or anti-CD19-APC coated beads are shown in gates P3 and P4, respectively. Unbound beads are visible in gate P2.

CHO cells stably transfected with membrane-bound TNFα (B-220 cells) (containing a mutant membrane-bound TNFα that contains a point mutation in the TACE cleavage site that prevents cleavage and shedding of TNFα ligand; see, for example, Scallon et al. J Pharmacol Exp Ther 2002; 301:418-26) were incubated with beads coated with a PE-labeled anti-TNFα antibody. In this set-up the beads mimic memory B cells. As negative controls, non-transfected CHO cells were used, as well as beads coated with an APC-labeled unrelated antibody (anti-CD19). After 2 hours incubation at 4° C. with agitation, the cell-bead suspension was analyzed by FACS (using a 130 um nozzle). FIG. 3 shows that a specific binding between anti-TNFα beads and TNFα-transfected CHO cells was clearly detectable with FACS. Indeed, in this sample (upper panel) about two thirds of the beads were bound to cells (585 bound against 267 unbound). In contrast, in the control samples (middle and lower panels), almost no bead bound to CHO cells. Further, both bead populations (anti-TNFα-PE and anti-CD19-APC) were mixed together with TNFα-transfected CHO cells. FIG. 4 shows that about half of the anti-TNFα beads bound to CHO cells, whereas the vast majority of the anti-CD19 beads stayed unbound. The percentage of beads binding to the cell in each sample is detailed in Table 2. Thus, the demonstration is made that the specific selection of single B cells that bind to an integral membrane target protein through their B cell receptor was possible using flow-cytometry.

TABLE 2

Percentage of beads bound to CHO cells in each sample

| | Cells | mAb on beads | % bound beads |
|---|---|---|---|
| Sample 1 | CHO-TNFα (B220) | anti-TNFα | 68.0 |
| Sample 2 | CHO-TNFα (B220) | anti-CD19 | 0.9 |
| Sample 3 | CHO wt | anti-TNFα | 1.5 |
| Sample 4 | CHO-TNFα (B220) | anti-TNFα | 47.0 |
| | | anti-CD19 | 0.4 |

TABLE 2a

Sorting statistics for upper panel of figure 3; binding of beads coated with anti-TNFα antibodies to TNFα-transfected CHO cells

| Population | # Events | % Parent | % Total |
|---|---|---|---|
| All Events | 10,000 | #### | 100.0 |
| P1 | 9,692 | 96.9 | 96.9 |
| P3 | 585 | 6.0 | 5.9 |
| P4 | 1 | 0.0 | 0.0 |
| P2 | 267 | 2.7 | 2.7 |

TABLE 2b

Sorting statistics for middle panel of figure 3; no binding of beads coated with anti-CD19 antibodies to TNFα-transfected CHO cells

| Population | # Events | % Parent | % Total |
|---|---|---|---|
| All Events | 10,000 | #### | 100.0 |
| P1 | 9,399 | 94.0 | 94.0 |
| P3 | 3 | 0.0 | 0.0 |
| P4 | 6 | 0.1 | 0.1 |
| P2 | 558 | 5.6 | 5.6 |

TABLE 2c

Sorting statistics for lower panel of figure 3; no binding of beads coated with anti-TNFα antibodies to CHO wildtype cells

| Population | # Events | % Parent | % Total |
|---|---|---|---|
| All Events | 10,000 | #### | 100.0 |
| P1 | 9,001 | 90.0 | 90.0 |
| P3 | 13 | 0.1 | 0.1 |
| P4 | 7 | 0.1 | 0.1 |
| P2 | 811 | 0.1 | 0.1 |

TABLE 2d

Sorting statistics for figure 4

| Population | # Events | % Parent | % Total |
|---|---|---|---|
| All Events | 10,000 | #### | 100.0 |
| P1 | 9,096 | 91.0 | 91.0 |
| P3 | 401 | 4.4 | 4.0 |
| P4 | 2 | 0.0 | 0.0 |
| P2 | 856 | 8.6 | 8.6 |

Example 3

Figure 5A:
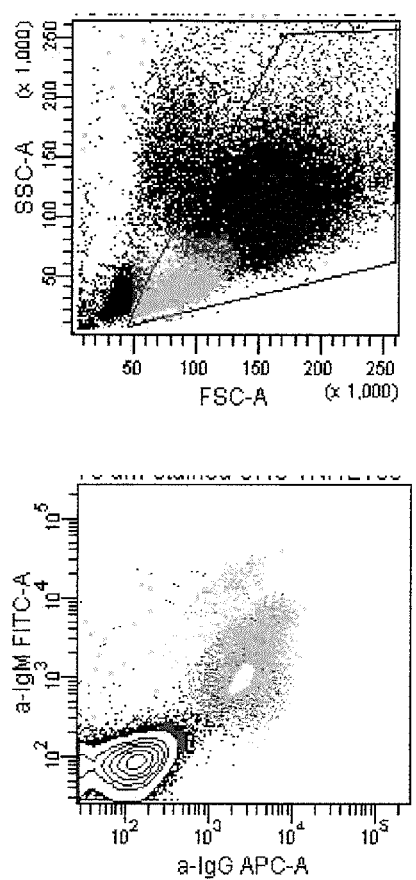
FIGS. 5A-5B.

Detection of the Interaction Between B Cell Isolated from an Anti-TNFα Antibody Immunized Rabbit and CHO Cells Expressing Membrane-Bound TNFα which were Saturated with Anti-TNFα Antibody For the experiment depicted in FIG. 5, lymphocytes were isolated either from an anti-TNFα antibody (ESBA105, produced in-house) immunized rabbit spleen or from a non-immunized rabbit spleen. They were stained with anti-rabbit IgG-APC and anti-rabbit IgM-FITC (AbD serotec) and subsequently pre-sorted in order to obtain pure populations of memory B cells (IgG+/IgM−). In parallel, TNFα-expressing CHO cells (donated by Dr. P Scheurich, Univ. of Stuttgart) were loaded with 1 ug/mL calcein-red (Invitrogen), a cytoplasmic dye that fluorescently stains living cells. These cells were then washed once and incubated with (or without, for the negative control) 100 ug/mL of ESBA105, and finally washed again 3× with PBS. Memory B cells were finally mixed at a ratio of about 1:10 with the CHO cells and incubated during 2 hours at 4° C. on a rotating plate (concentration: $3*10^7$ cells/mL). The following samples were prepared:
1) CHO-TNFα cells+ESBA105+ memory B cells of ESBA105 immunized rabbit
2) CHO-TNFα cells+ESBA105+memory B cells of non-immunized rabbit
3) CHO-TNFα cells+memory B cells of ESBA105 immunized rabbit After 2 hours incubation, the 3 samples were measured by FACS, using the 70 um nozzle. According to the population hierarchy shown in Table 3a, 5% of ESBA105 immunized cells bind to "ESBA105-coated" TNFα transgenic CHO cells. In comparison, only 0.5% non-immunized B cell bind to these"ESBA105-coated" TNFα transgenic CHO cells (Table 3b), and 0.6% of immunized B cells bind in absence of ESBA105 on CHO cell surface (Table 3c). These results give a show that a specific interaction between a BCR (B cell receptor) and a transmembrane target can be detected by FACS.

TABLE 3a

Figure 5B:
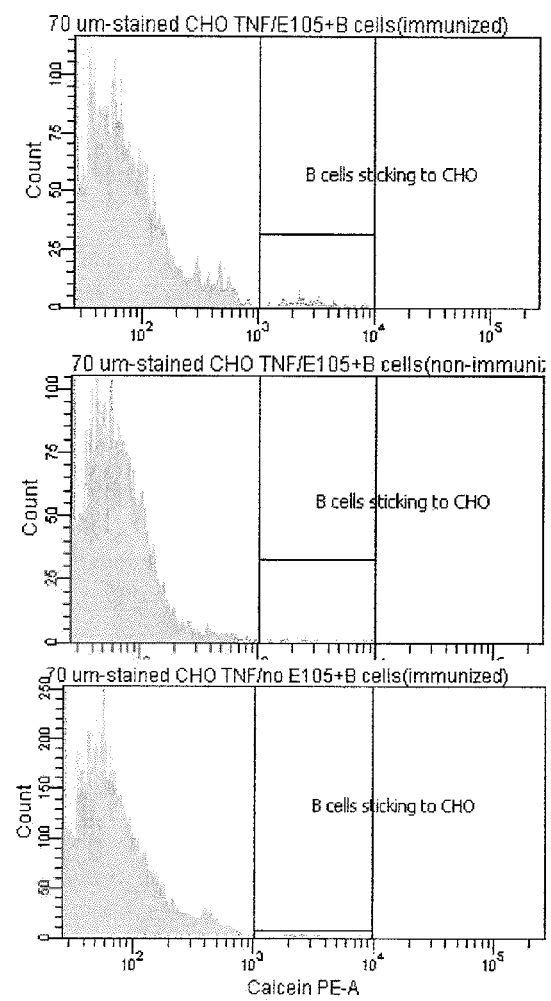

Sorting statistics for upper panel of FIG. 5b

| Population | #Events | % Parent | % Total |
|---|---|---|---|
| All Events | 50,000 | #### | 100.0 |
| Living cells | 43,828 | 87.7 | 87.7 |
| B cells | 5,162 | 11.8 | 10.3 |
| B cells sticking to CHO | 78 | 1.5 | 0.2 |

TABLE 3b

Sorting statistics for middle panel of FIG. 5b

| Population | #Events | % Parent | % Total |
|---|---|---|---|
| All Events | 50,000 | #### | 100.0 |
| Living cells | 43,834 | 87.7 | 87.7 |
| B cells | 4,290 | 9.8 | 8.6 |
| B cells sticking to CHO | 23 | 0.5 | 0.0 |

TABLE 3c

Sorting statistics for lower panel of FIG. 5b

| Population | #Events | % Parent | % Total |
|---|---|---|---|
| All Events | 50,000 | #### | 100.0 |
| Living cells | 42,982 | 86.0 | 86.0 |
| B cells | 10,150 | 23.6 | 20.3 |
| B cells sticking to CHO | 65 | 0.6 | 0.1 |

Example 4

Detection of the Interaction Between B Cell Isolated from an ESBA105 Immunized Rabbit and CHO Cells Expressing Membrane-Bound TNFα which were Saturated with ESBA105

Figure 6A:
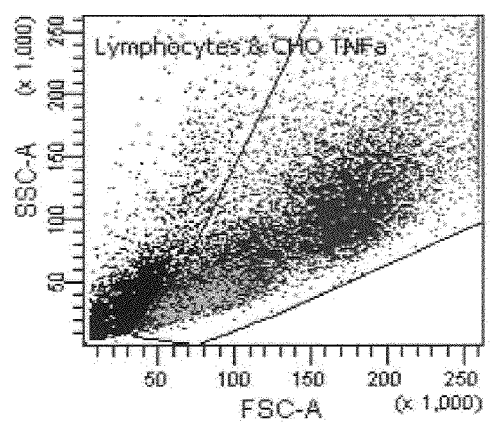
FIGS. 6A-6C: FACS analysis of the suspension consisting of immunized lymphocytes mixed with TNFα transgenic CHO cells "coated" with ESBA105.
Figure 6B:
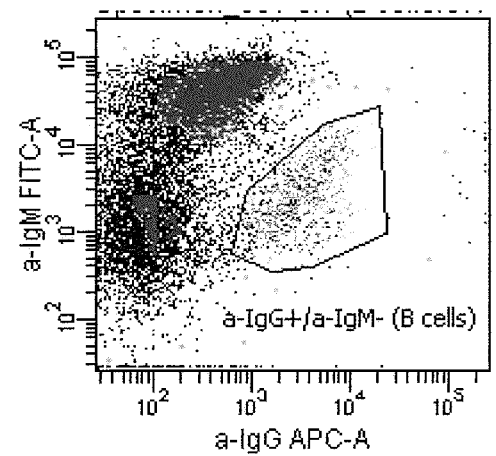
Figure 6C:
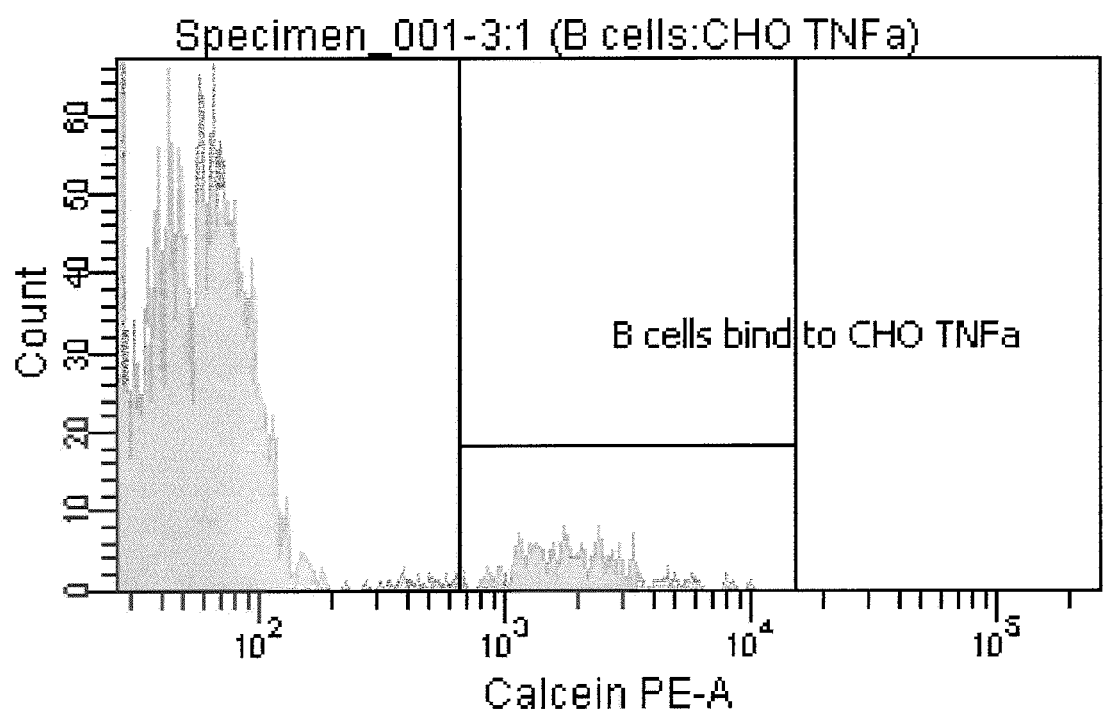

In a further experiment, no pre-sorting of memory B cells was made. The entire lymphocyte population was incubated with the stained CHO-TNFα-ESBA105 cells. Transgenic CHO cells were prepared as described above. However, in order to prevent their proliferation in B cell culture medium after the sort in 96-well plates, the cells were cell-cycle arrested by a mitomycin C (M4287-2MG) treatment before the calcein staining The lymphocytes of an ESBA105 immunized rabbit were mixed at a ratio of 3:1 with the stained CHO cells (concentration of the cell suspension: ≈$3$-$10^7$ cells/mL), and incubated during 2 hours at 4° C. on a rotating plate. After this, the cell suspension was FACS analyzed and memory B cells binding to CHO-TNFα-ESBA105 were sorted according to the gate depicted in FIG. 6, with 1, 10 or 100 cells/well as shown in Table 3. Sorted cells represented 5.5% of the memory B cell population, respectively 0.2% of total events.

Sorted cells were collected in 96-well plates and cultivated during 13 days at 37° C. with 5% $CO_2$. After that, culture supernatants were collected and tested in direct ELISA to check for the presence of ESBA105 binding IgGs. ELISA results (Table 3) show that ESBA105 specific antibodies could be detected in many wells, and also in wells where single B cells were sorted. The Biacore (GE Healthcare) analysis (Table 4) of these supernatants confirmed that these antibodies indeed bound to ESBA105 target.

TABLE 3

ELISA analysis of B cell culture supernatant samples taken 13 days after sorting.

| Day 13 | | 0 B cell/well | | | | | | | | | Positive control | |
|---|---|---|---|---|---|---|---|---|---|---|---|---|
| ◇ | 1 | 2 | 3 | 4 | 5 | 6 | 7 | 8 | 9 | 10 | 11 | 12 |
| A | 0.0690 | 0.0680 | 0.0600 | 0.0470 | 0.0540 | 0.0700 | 0.0660 | 0.0750 | 0.0490 | 0.0690 | 2.7270 | 2.7020 |
| B | 0.0660 | 0.0630 | 2.7190 | 0.0460 | 0.0500 | 0.0640 | 0.0630 | 0.0770 | 2.7920 | 0.0580 | 2.8670 | 2.8880 |
| C | 0.0700 | 2.8380 | 0.0520 | 0.0470 | 0.0540 | 0.0690 | 2.9260 | 2.7160 | 0.0570 | 0.0690 | 2.9500 | 2.7730 |
| D | 0.0680 | 0.0630 | 0.0560 | 0.0490 | 0.0520 | 0.0640 | 0.0650 | 0.7840 | 0.4480 | 0.0620 | 3.0010 | 2.9250 |
| E | 0.0750 | 0.0730 | 0.0630 | 0.0550 | 0.0630 | 0.0670 | 2.8550 | 0.0830 | 0.0580 | 1.9820 | 2.1250 | 2.8090 |
| F | 0.0680 | 0.0640 | 2.7090 | 0.0530 | 0.0580 | 0.0680 | 0.0750 | 2.5610 | 0.0610 | 0.3820 | 2.8150 | 2.8180 |
| G | 0.0820 | 0.0740 | 0.0660 | 1.7530 | 0.0700 | 0.0780 | 0.3980 | 0.0740 | 2.8920 | 1.8240 | 2.7910 | 2.7510 |
| H | 0.0730 | 0.0680 | 0.0620 | 0.0570 | 0.0610 | 0.0720 | 0.1710 | 1.9590 | 0.0610 | 2.7830 | 0.1800 | 2.8510 |
| | | | 1 B cell/well | | | | | 10 B cells/well | | | 100 B cells/well | |

No B cells were sorted in raw A wells in order to verify specificity of OD450 signals. In wells A11 and A12, a polyclonal rabbit anti-ESBA105 antibody (AK3A; 2 ug/mL) was spiked in supernatant as positive control. Wells where OD450 is significantly higher than background are highlighted in bold.

TABLE 4 kinetic values and concentrations determined by Biacore for the B cell culture supernatants.

| Protein | Ka (1/Ms) | Kd (1/s) | % SE (ka) | % SE (kd) | KD (M) | Fitted Rmax (RU) | Chi2 (% of Rmax) | Capture level Bcell medium with IgGs | Capture level B cell medium | Approximate net capture level | Concentration (ug/ml) |
|---|---|---|---|---|---|---|---|---|---|---|---|
| 19-01-B3 | 1.54E+06 | 2.83E−03 | 0.29 | 0.20 | 1.8E−09 | 64.0566 | 0.30 | 772.65 | 554.36 | 218.30 | 0.273 |
| 19-01-C2 | 2.30E+09 | 3.23E+01 | 0.04 | 0.04 | 1.4E−08 | 99.0582 | 10.46 | 1069.06 | 546.00 | 523.06 | 1.576 |
| 19-01-F3 | 1.46E+06 | 2.31E−03 | 0.30 | 0.20 | 1.6E−09 | 77.848 | 0.37 | 803.86 | 537.13 | 266.72 | 0.347 |
| 19-01-G4 | 3.40E+06 | 4.45E−03 | 2.86 | 2.29 | 1.3E−09 | 4.43221 | 1.43 | 578.01 | 548.58 | 29.43 | BQL |
| 19-02-B4 | 8.18E+05 | 3.18E−03 | 0.22 | 0.15 | 3.9E−09 | 80.3549 | 0.22 | 822.67 | 539.30 | 283.37 | 0.397 |
| 19-02-D3 | 1.01E+06 | 2.95E−03 | 0.54 | 0.36 | 2.9E−09 | 23.7639 | 0.41 | 652.51 | 547.28 | 105.23 | 0.066 |
| 19-02-F2 | 2.61E+06 | 6.61E−04 | 1.53 | 0.59 | 2.5E−10 | 12.533 | 0.64 | 5214.04 | 514.43 | 9.61 | BLQ |

Only supernatants where one cell per well was sorted were measured. BLQ: below limit of quantification Example 5

Screening of Lymphocytes of Rabbits Immunized with CXCR2

Sorts 27/29

Three rabbits were immunized with a CXCR2 expression vector. After several intradermal applications of CXCR2-cDNA, serum was taken and tested on CXCR2 transfected cells for presence of specific antibodies. Lymph node cells were then removed, frozen in five aliquots with each $1.6 \times 10^7$ cells and were stored in a liquid nitrogen tank.

An aliquot was thawed and stained with antibodies specific for IgG (APC-labeled) or IgM (FITC labeled). In parallel, CXCR2-expressing CHO cells were treated with mitomycin C, in order to prevent further growth without killing the cells, and loaded with 1 ug/mL calcein-red. Both cell preparations were then mixed with a final cell concentration of $10^7$ cells/ml, lymphocytes being twice as abundant as CXCR2-transfected CHO cells. After 2 hour incubation with gentle agitation at 4° C., cell suspension was filtered through a 50-um filter and loaded on the FACS. Gating was performed as described in FIG. 6. One "event" (Memory B cells bound to a CXCR2-transfected CHO cell) was sorted per well in a total of 10×96-well plates (900 events in total). Sorted events represented 3.1% of the memory B cell population, respectively 0.035% of total cell amount in the sample.

Selected lymphocytes were cultivated during 21 days in a 37° C. incubator. Every 2-3 days, 100 uL of culture supernatant were collected from the wells and replaced by fresh medium. During this culture time, B cells proliferated, differentiated into plasma cells and secreted antibodies. In order to visualize which supernatants contained CXCR2 specific antibodies, a CELISA was performed. For this, CHO cells expressing CXCR2 were seeded at a density of 50,000 cells/well in 96-well half area plates. After overnight incubation at 37° C., cells were fixed with 1% formaldehyde in PBS for 30 minutes at room temperature. Cell layers were then washed three times and non specific binding sites were blocked with cell culture medium during one hour at room temperature. Next, after three washing steps, the supernatants were diluted 1:1 in culture medium and added to the wells. In three control wells, a commercial rabbit anti-CXCR2 antibody was spiked in supernatant. Supernatants were incubated on the cell layers during one and a half hour at room temperature. Finally, rabbit IgGs were detected with a goat anti-rabbit IgG Fc antibody coupled to HRP. Upon addition of a peroxidase substrate (Blue POD substrate from Roche), a colorimetric reaction developed which was stopped after 25 minutes with 1M HCl. Absorbance was measured at 450 nm.

This CELISA resulted in 1.8% of wells (16/900) displaying positive signals. All positives were confirmed in a second CELISA. Supernatants were also tested against other cell lines: CHO-K1 (wild type) to reveal eventual unspecific binding clones, CHO-human CXCR1 and CHO-mouse CXCR2 to demonstrate cross-activity against close-related receptor or species counterpart. Finally, supernatants were tested in a direct ELISA for binding to a peptide consisting of the 48 CXCR2 N-terminal amino acids. Results are displayed in Table 5. All selected supernatants produced strong $OD_{450}$ signals against human CXCR2 in CELISA. Some of them were also slightly positive in the control experiment with the CHO wild type cells, meaning that they might bind in an unspecific way. None of the clones was cross-reactive with human CXCR1 or mouse CXCR2. Finally, some clones, but not all of them, bound to the CXCR2 N-terminal peptide, indicating a probable alternative binding site on CXCR2. Given the impossibility of immobilizing entire cells on a Biacore chip, it is currently impossible to quantitatively measure the affinity of selected antibodies for CXCR2 receptor. However, gathered data converge to indicate that antibodies specific to human CXCR2 were selected using the cell-cell interaction sorting system described above.

TABLE 5

Summary of CELISA results from anti-CXCR2 clones isolated during sort 27 and 29

| | direct CELISA against CXCR2 | | | rabbit IgG | CELISA | CELISA | ELISA N- |
|---|---|---|---|---|---|---|---|
| Clone number | 1. Assay $OD_{450}$ | 2. Assay $OD_{450}$ | CHO wt. $OD_{450}$ | quantification in ELISA (ng/mL) | CXCR1 $(OD_{450})$ | mCXCR2 $(OD_{450})$ | term $(OD_{450})$ |
| 27-01-E3 | 3.3576 | 3.384 | 0.199 | 13501.9 | 0.1111 | 0.2210 | 2.3224 |
| 27-01-D9 | 3.1769 | 3.652 | 0.084 | 431.6 | 0.1100 | 0.1081 | 2.1632 |
| 27-01-H9 | 3.2068 | 3.707 | 0.366 | 6439.8 | 0.3410 | 0.3180 | 0.0552 |
| 27-02-D3 | 2.1209 | 2.971 | 0.090 | 370.2 | 0.1190 | 0.1169 | 0.0507 |
| 27-03-H4 | 3.4092 | 3.490 | 0.373 | 904.3 | 0.4470 | 0.2562 | 2.7145 |
| 27-04-B3 | 2.7205 | 3.284 | 0.410 | 2896.1 | 0.4810 | 0.2724 | 0.0602 |
| 27-06-B5 | 0.4456 | 0.457 | 0.091 | <5 ng/ml | 0.1050 | 0.0980 | 0.05 |
| 27-06-A6 | 3.2461 | 3.507 | 0.423 | 1259 | 0.3640 | 0.2119 | 2.1627 |
| 27-07-B2 | 3.2434 | 3.390 | 0.140 | 455.9 | 0.1210 | 0.1216 | 2.4233 |
| 27-08-D5 | 3.1386 | 3.302 | 0.090 | 178.4 | 0.1060 | 0.0910 | 2.2873 |
| 27-08-G9 | 3.3705 | 3.302 | 0.100 | 427.6 | 0.1160 | 0.0881 | 2.4506 |
| 27-08-G11 | 3.2857 | 3.380 | 0.125 | 2755 | 0.1660 | 0.1389 | 0.2955 |
| 27-09-A1 | 0.9547 | 1.926 | 0.103 | 261.1 | 0.1180 | 0.0996 | 0.0383 |
| 27-09-D1 | 3.2530 | 3.503 | 0.094 | 1576.5 | 0.1210 | 0.1238 | 0.0504 |
| 27-09-A5 | 3.2953 | 3.501 | 0.482 | 4502 | 0.4970 | 0.2491 | 2.5863 |
| 27-10-C3 | 0.6464 | 1.522 | 0.092 | 35.5 | 0.1030 | 0.1080 | 0.0513 |
| 29-01-H10 | 3.3345 | 3.3405 | 0.1558 | 5238.5 | 0.1810 | 0.1644 | 2.5374 |
| 29-02-C4 | 3.1456 | 3.3931 | 0.1219 | 2406.9 | 0.1490 | 0.1513 | 2.5126 |
| 29-02-H8 | 3.4441 | 3.3891 | 0.1178 | 4645.7 | 0.1260 | 0.1287 | 2.4003 |
| 29-02-C10 | 3.1259 | 3.4947 | 0.1128 | 861.3 | 0.1220 | 0.1074 | 1.9841 |
| 29-03-G11 | 2.5987 | 3.0270 | 0.1181 | 420.1 | 0.1110 | 0.0828 | 0.0501 |
| 29-04-F11 | 3.0250 | 3.1871 | 0.2768 | 16071.6 | 0.3160 | 0.1999 | 2.6047 |
| 29-05-E11 | 3.5481 | 3.4769 | 0.1531 | 2857.3 | 0.1950 | 0.1081 | 2.2094 |
| 29-06-H3 | 3.4308 | 3.4005 | 0.1254 | 8741.7 | 0.1530 | 0.1489 | 2.6543 |
| 29-06-D10 | 3.3152 | 3.4020 | 0.1316 | 1522.1 | 0.1210 | 0.1101 | 2.4598 |
| 29-07-H4 | 3.3693 | 3.4622 | 0.8502 | 16580.3 | 1.5030 | 0.7195 | 2.4458 |
| 29-08-E1 | 3.7283 | 3.4990 | 1.0667 | 10562.2 | 1.4780 | 0.5225 | 2.3015 |
| 29-08-G10 | 2.8429 | 2.5070 | 0.1107 | 40.4 | 0.1110 | 0.0955 | 1.8621 |
| 29-09-C4 | 1.1362 | 0.8767 | 0.1054 | <5 ng/ml | 0.1090 | 0.0900 | 0.3539 |

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

What is claimed is:

1. A method for identifying an immunobinder that specifically binds to a cell surface antigen of interest comprising:
   (a) providing a plurality of immunobinder-expressing cells comprising a first sortable label;
   (b) providing a plurality of antigen-expressing cells comprising a second sortable label, wherein the antigen of interest is displayed at the surface of the antigen-expressing cell;
   (c) contacting the antigen-expressing cells with the immunobinder-expressing cells; and
   (d) separating from the plurality of immunobinder-expressing cells, one or more immunobinder-expressing cells that can specifically bind to the antigen expressing cells using a cell sorter, wherein the presence of the first and second sortable label in a single cellular complex is indicative of the binding of an immunobinder-expressing cell to an antigen-expressing cell, thereby identifying an immunobinder that binds to a antigen of interest.

2. The method of claim 1, further comprising clonally isolating the immunobinder-expressing cells obtained in step (d), optionally followed by clonal expansion of the clonally isolated cells.

3. The method of claim 2, further comprising obtaining the immunobinder-encoding nucleic acid sequence from the isolated immunobinder-expressing cells.

4. The method of claim 2, further comprising subjecting the isolated immunobinder-expressing cells to a cell-based assay to functionally characterize the immunobinder.

5. The method of claim 1, wherein the immunobinder is an antibody.

6. The method of claim 5, wherein the antibody is a mouse, rabbit, chicken, camel, human, humanized, or chimeric antibody.

7. The method of claim 6, wherein the antibody is a full length immunoglobulin, Fab, Dab, scFv, or Nanobody.

8. The method of claim 1, wherein the antigen of interest is expressed from an exogenous gene.

9. The method of claim 1, wherein the antigen of interest is a genetically engineered antigen expressed from an expression vector.

10. The method of claim 1, wherein the antigen of interest is an integral membrane protein.

11. The method of claim 10, wherein the integral membrane protein is a GPCR or an ion channel.

12. The method of claim 11, wherein the GPCR is CXCR2, CXCR1, CXCR3, CXCR4, CXCR6, CCR1, CCR2, CCR3, CCR4, CCR5, CCR6, CCR8, CFTR, CIC-1, CIC-2, CIC-4, CIC-5, CIC-7, CIC-Ka, CIC-Kb, Bestrophins, TMEM16A, GABA receptor, glycin receptor, ABC transporters, NAV1.1, NAV1.2, NAV1.3, NAV1.4, NAV1.5, NAV1.6, NAV1.7, NAV1.8, NAV1.9, sphingosin-1-phosphate receptor (S1P1R) or NMDA channel.

13. The method of claim 1, wherein the first or second sortable label is a fluorescent label.

14. The method of claim 13, wherein the fluorescent label is a fluorescent protein, an antibody/fluor conjugate, or a fluorescent cellular label.

15. The method of claim 1, wherein the antigen-expressing cells are yeast cells, yeast spheroblasts or mammalian cells.

16. The method of claim 15, wherein the antigen-expressing cells are human cells.

17. The method of claim 1, wherein the immunobinder-expressing cells are yeast or mammalian cells.

18. The method of claim 1, wherein the immunobinder-expressing cells are B-cells.

19. The method of claim 18, wherein the B-cells are rabbit 13-cells.

20. The method of claim 18, wherein the B-cells are isolated from an immunized animal.

21. The method of claim 20, wherein the animal is immunized by DNA vaccination.

22. The method of claim 1, wherein the immunobinder-expressing cells comprise an immunobinder expressed from an expression vector.

* * * * *